US006602680B2

(12) United States Patent
Rubenstein et al.

(10) Patent No.: US 6,602,680 B2
(45) Date of Patent: Aug. 5, 2003

(54) PRODUCTION OF GABAERGIC CELLS

(75) Inventors: John L. Rubenstein, San Francisco, CA (US); Marina Mione, London (GB); Stewart Anderson, San Francisco, CA (US); Thorsten Stuehmer, San Francisco, CA (US); Kyuson Yun, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/900,527

(22) Filed: Jul. 5, 2001

(65) Prior Publication Data

US 2002/0151066 A1 Oct. 17, 2002

Related U.S. Application Data

(60) Provisional application No. 60/218,221, filed on Jul. 14, 2000.

(51) Int. Cl.⁷ ............................ C12Q 1/68; C12Q 1/02; C12N 15/85
(52) U.S. Cl. .......................... 435/29; 435/6; 435/320.1; 435/455; 536/23.1; 536/23.2; 536/23.5; 424/93.7
(58) Field of Search ......................... 435/6, 320.1, 455, 435/29; 536/23.1, 23.2, 23.5; 424/93.7

(56) References Cited

U.S. PATENT DOCUMENTS

| | | |
|---|---|---|
| 5,324,638 A | 6/1994 | Tao et al. |
| 5,411,883 A | 5/1995 | Boss et al. |
| 5,589,376 A | 12/1996 | Anderson et al. |
| 5,639,618 A | 6/1997 | Gay |
| 5,824,489 A | 10/1998 | Anderson et al. |
| 5,958,767 A | 9/1999 | Snyder et al. |
| 5,968,829 A | 10/1999 | Carpenter |
| 5,979,872 A | 11/1999 | Stearns et al. |

FOREIGN PATENT DOCUMENTS

WO    WO 00/45840    8/2000

OTHER PUBLICATIONS

Cooper et al. (1970) in The Biochemical Basis of Neuropharmacology, Oxford University Press, pp. 11–13.*
Principals of Neural Science, Fourth Edition, (Kandel et al. eds.) McGraw–Hill, New York, Figure 14–13.*
Finley et al. Synapse formation and establishment of neuronal polarity by P19 embryonic carcinoma cells and embryonic stem cells. J Neurosci. 1996 Feb. 1;16(3): 1056–65.*
Inder M. Verma et al, Gene therapy–promises, problems and prospects, Nature vol. 389, Sep. 18, 1997.*
E. Marshall, Gene Therapy's Growing Pains, Science vol. 269, Aug. 25, 1995.*
Stuart H. Orkin et al, Report And Recommendations Of The Panel To Assess The NIH Investmenst In Research On Gene Therapy, Dec. 7, 1995.*
Gail Ross et al, Special feature, Human Gene Therapy 7:1781–1790 Sep. 10, 1996.*
Stuhmer, et al., "Ectopic Expression of the Dlx Genes Induces Glutamic Acid Decarboxylase and Dlx Expression", Development 129, 245–252 (2002).
Stuhmer, et al., "Expression from a Dlx Gene Enhancer Marks Adult Mouse Cortical GABAergic Neurons", Cerebral Cotex 12:75–85 (2002).
Anderson et al. (1997), "Mutations of the Homeobox Genes Dlx–1 and Dlx–2 Disrupt the Striatal Subventricular Zone and Differentiation of Late Born Striatal Neurons", Neuron, 19:27–37, Cell Press.
Anderson et al., (1997) "Interneuron Migration from the Basal Forebrain to Neocotex: Dependence on Dlx Genes", Science, 278:474–476.
Anderson et al., (1999) "Differential Origins of Neocortical Projection and Local Circuit Neurons: Role of Dlx Genes in Neocortical Interneuronogenesis", Cereb. Cortex, 6:646–54, Oxford Univ. Press.
Anderson et al (1989) "Cloning, Structure, and Expression of the Mitochondrial Cytochrome P–450 Sterol 26–Hydoxylase, a Bile Acid Biosythetic Enzyme", J. Biol. Chem. 264(14):8222–8229, Cell Press.
Briscoe et al., (Nov. 2000) "A Homeodomain Protein Code Specifies Progenitor Cell Identity and Neuronal Fate in the Ventral Neural Tube", Cell 101:435–445.
Bulfone et al. (1993) "Spatially Restricted Expression of Dlx–1 (Tes–1), Gbx–2, and Wnt–3 in the Embryonic Day 12.5 Mouse Forebrain Defines Potential Transverse and Longitudinal Segmental Boundaries", J. Neurosci. 13(7): 3155–3172.
Bulfone et al. (1993) "The mouse Dlx–1 (Tes–1) gene is expressed in spatially restructed domains of the forebrain, face and limbs in midgestation mouse embryos", Mech. Dev. 40:129–140.
Buflone et al. (1998) "An Olfactory Sensory Map Develops in the Absence of Normal Projection Neurons or GABAergic Interneurons", Neuron, 21:1273–1282.

(List continued on next page.)

Primary Examiner—James Ketter
Assistant Examiner—Daniel Sullivan
(74) Attorney, Agent, or Firm—Carol L. Francis; Paula A. Borden; Bozicevic, Field & Francis, LLP

(57) ABSTRACT

The invention features methods and compositions for the production of GABAergic cells, particularly GABAergic neurons. Production of GABAergic cells is accomplished by increasing activity of a Dlx gene (e.g., DLX1, DLX2, or DLX5) in an immature neuronal cell. The increase in Dlx activity causes differentiation of the immature neuronal cell into a neuronal cell exhibiting the GABAergic phenotype. The invention also encompasses use of GABAergic cells produced by the method of the invention in, for example, identification of agents that affect GABAergic cell activity and survival, and in replacement therapy.

7 Claims, 7 Drawing Sheets

OTHER PUBLICATIONS

Casarosa S. et al. (1999) "Mash 1 regulates neurogenesis in the ventral telencephalon", Development, 126(3):525–34.

Cavanagh et al. (1997) "Basic Fibroblast Growth Factor Prolongs the Proliferation of Rat Cortical Progenitor Cells In Vitro without Altering Their Cell Cycle Parameters", Cerebral Cortex 7:293–302.

De Carlos et al. (1996) "Dynamics of Cell Migration from the Lateral Ganglionic Eminence in the Rat", J. Neurosci. 16(19):6146–6156.

Dediego et al. (1994) "Cortical Cells That Migrate Beyond Area Boundaries: Characterization of an Early Neuronal Population in the Lower Intermediate Zone of Prenatal Rats", Eur. J. Neurosci. 6:983–997.

Depew, M. J. et al. (1999) "Dlx5 regulates regional development of the branchial arches and sensory capsules", Development, 126(17): 3831–3846.

Eisenstat et al. (1999) "DLX–1, DLX–2, and DLX–5 Expression Define Distinct Stages of Basal Forebrain Differentiation", J. Comp. Neurol. 414:217–237.

Ferrari et al. (1999) "Dlx–5 in Lib Initiation in the Chick Embryo", Developmental Dynamics 216(1):10–15.

Funahashi et al. (1999) "Role of Pax–5 in the regulation of a mid–hindbrain organizer's activity", Dev. Growth Differ. 41:59–72.

Gadisseux et al. (1992) "The Human Transient Subpial Granular Layer: An Optical, Immunohistochemical and Ultrastructural Analysis", J. Comparative Neurol. 324:94–114.

Garcia–Alonso et al., (1992) "The EGF and FGF Receptors Mediate Neuroglian Function to Control Growth Cone Decisions during Sensory Axon Guidance in Drosophila", Neuron 28:741–751.

Genbank Accession No. NM 010054.

Genbank Accession No. U51002.

Hevner et al. (2001) "Tbr1 Regulates Differentiation of the Preplate and Layer 6", Neuron 29:353–366.

Kinsella et al. (1996) "Episomal Vectors Rapidly and Stably Produce High–Titer Recombinant Retrovirus", Human Gene Therapy, 7(12):1405–13.

Kohtz et al., (1998) "Regionalization within the mammalian telencephalon is mediated by changes in responsiveness to Sonic Hedgehog", Development 125:5079–5089.

Lavdas et al., (1999) "The Medial Ganglionic Eminence Gives Rise to a Population of Early Neurons in the Developing Cerebral Cortex", J. Neurosci. 19:7881–7888.

Liu et al., (1997) "Dlx Genes Encode DNA–Binding Proteins That are Expressed in an Overlapping and Sequential Pattern During Basal Ganglia Differentiation," Dev. Dyn. 210:498–512.

Lois and Alvarez–Buylla (1994) "Long–Distance Neuronal Migration in the Adult Mammalian Brain", Science 264: 1145–1148.

Luskin (1993) "Restricted Proliferation and Migration of Postnatally Generated Neurons Derived from the Forebrain Subventricular Zone", Neuron 11:173–189.

Marín et al. (2000) "Origin and Molecular Specification of Striatal Interneurons", J. Neurosci. 20(16): 6063–6076.

McGuinness et al. (1996) "Sequence, Organization, amd Transcription of the dlx–1 and Dlx–2 Locus", Genomics 35:473–485.

Meyer et al. (1998) "Different Origins and Developmental Histories of Transient Neurons in the Marginal Zone of the Fetal and Neonatal Rat Cortex", J. Comp. Neurol. 397:493–518.

Niwa et al. (1991) "Efficient selection for high–expression transfectants with a novel eukaryotic vector", Gene 108:193–199.

Parnavelas, J. G. (2000) "The origin and migration of cortical neurons: new vistas", Trends Neurosci. 23: 126–131.

Pleasure et al. (2000) "Cell Migration from the Ganglionic Eminences Is Required for the Development of Hippocampal GABAergic Interneurons", Neuron 28:727–740.

Porteus et al., (1991) "Isolation and Characterization of a Novel cDNA Clone Encoding a Hoeodomain That is Developmentally Regulated in the Ventral Forebrain", Neuron 7:221–229, Cell Press.

Porteus et al. (1992) "Isolation and characterization of a library of cDNA clones that preferentially expressed in the embryonic telencephalon", Mol. Brain Res. 12:7–22.

Porteus et al., (1994) "DLX–2, MASH–1, and MAP–2 Expression and Bromodeoxyuridine Incorporation Define Molecularly Distinct Cell Populations in the Embryonic Mouse Forebrain", J. Neurosci. 14(11): 6370–6383.

Price et al. (1991) "A mouse gene related to Distal–less shows a restricted expression in the developing forebrain", Nature 351:748–751.

Qiu et al. (1997). "Null mutation of DLX–2 results in abnormal morphogeneis of proximal first and second branchial arch derivatives and abnormal differentiation in the forebrain", Genes Dev. 9:2523–2538.

Rubenstein et al. (1998) "Regionalization of the Prosencephalic Neural Plate", *Annu. Rev. Neurosci.*, 21:445–77.

Rubenstein et al. (1998) "Patterning of the embryonic forebrain", *Current Opinion in Neurobiology*, 8:18–26.

Sander et al. (2000) "Ventral neural patterning by Nkx homeobox genes: Nkx6.1 control somatic motor neuron and ventral interneuron fates", Genes Dev. 14:2134–2139.

Shimamura et al. "Inductive interactions direct early regionalization of the mouse forebrain", Development 124:2709–2718.

Simeone et al. (1994) "Cloning and characterization of two members of the vertabrate Dlx gene family", Proc. Natl. Acad. Sci. USA 91:2250–2254.

Stock et al. (1996) "The evolution of the vertebrate Dlx gene family", Proc. Natl. Acad. Sci. USA 93:10858–10863.

Sussel et al., (1999) "Loss Of Nkx2.1 Homeobox Gene Function Results in a Ventral to Dorsal Molecular Respecification Within The Basal Telencephalon: Evidence for a Transformation of the Pallidum Into the Striatum", Development 126:3359–3370.

Tamamaki et al. (1997) "Origin and Route of Tangentially Migrating Neurons in the Developing Neocortical Intermediate Zone", J. Neurosci. 17:8313–8323.

Wichterle et al. (1999) "Young neurons from medial ganglionic eminence disperse in adult and embryonic brain", Nat. Neuroscl. 2:461–466.

Zerucha et al. (2000) "A Highly Conserved Enhancer in the Dlx5/Dlx6 Intergenic Region is the Site of Cross–Regulatory Interactions between Dlx Genes in the Embryonic Forebrain", J. Neurosci. 20:709–721.

* cited by examiner

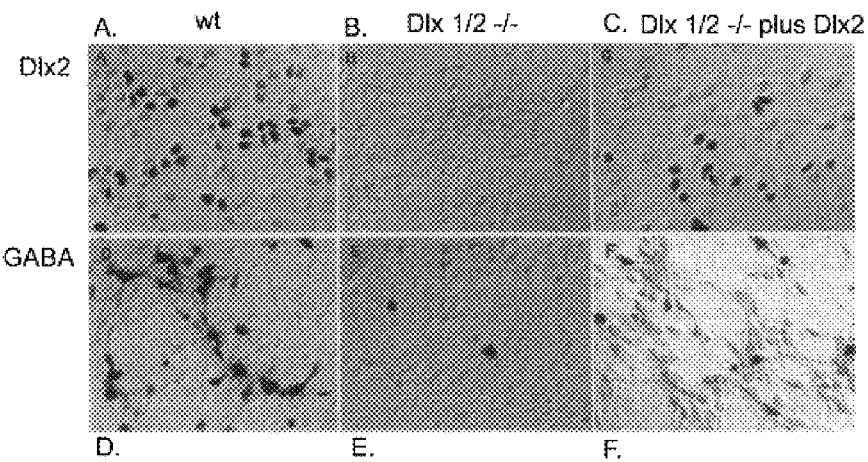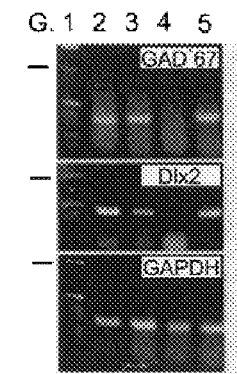
FIG. 1A  FIG. 1B  FIG. 1C
FIG. 1D  FIG. 1E  FIG. 1F  FIG. 2

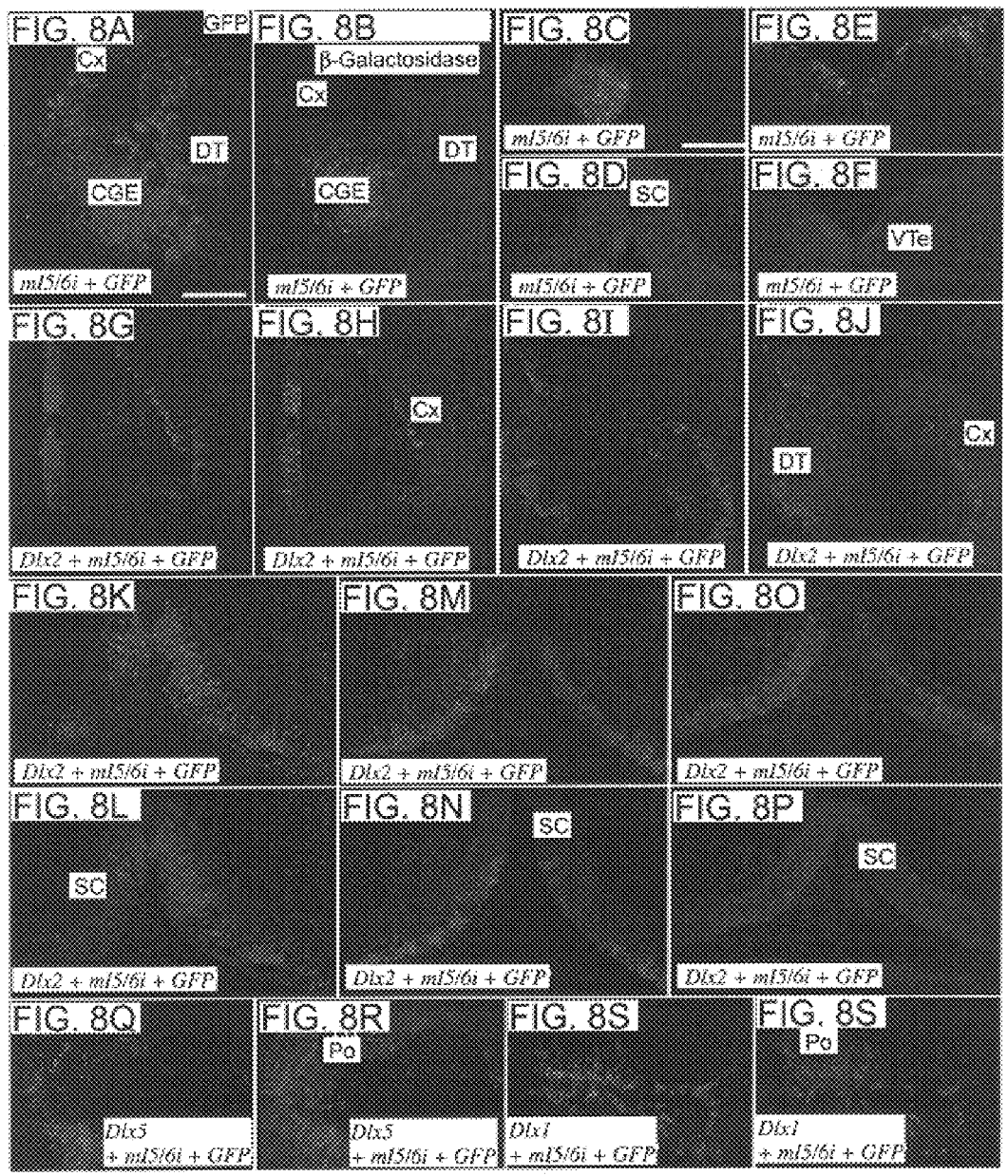

SEQUENCE LISTING

<160> NUMBER OF SEQ ID NOS: 8

<210> SEQ ID NO 1
<211> LENGTH: 2091
<212> TYPE: DNA
<213> ORGANISM: Homo sapiens

<400> SEQUENCE: 1

| | | | | | |
|---|---|---|---|---|---|
| atgactggag | tctttgacag | tctagtggct | gatatgcact | cgacccagat | cgccgcctcc | 60 |
| agcacgtacc | accagcacca | gcagcccccg | agcggcggcg | gcgccggccc | gggtggcaac | 120 |
| agcagcagca | gcagcagcct | ccacaagccc | caggagtcgc | ccaccttcc | ggtgtccacc | 180 |
| gccaccgaca | gcagctacta | caccaaccag | cagcacccgg | cgggcggcgg | cggcggcggg | 240 |
| ggctcgccct | acgcgcacat | gggttcctac | cagtaccaag | ccagcggcct | caacaacgtc | 300 |
| ccttactccg | ccagagcag | ctatgacctg | gctacaccg | ccgcctacac | ctcctacgct | 360 |
| ccctatggaa | ccagttcgtc | cccagccaac | aacgagcctg | agaaggagga | ccttgagcct | 420 |
| gaaattcgga | tagtgaacgg | gaagccaaag | aaagtccgga | accccgcac | catctactcc | 480 |
| agtttccagc | tggcggctct | tcagcggcgt | ttccaaaaga | ctcagtactt | ggccttgccg | 540 |
| gagcgagccg | agctggcggc | ctctctgggc | ctcacccaga | ctcaggtcaa | aatctggttc | 600 |
| cagaaccgcc | ggtccaagtt | caagaagatg | tggaaaagtg | gtgagatccc | ctcggagcag | 660 |
| caccctgggg | ccagcgcttc | tccaccttgt | gcttcgccgc | cagtctcagc | gccggcctcc | 720 |
| tgggactttg | tgtgtccgca | gcggatggcg | gcggcggtg | gtccgggcag | tggcggcagc | 780 |
| ggcgccggca | gctcgggctc | cagcccgagc | agcgcggcct | cggcttttct | gggcaactac | 840 |
| ccctggtacc | accagaccctc | gggatccgcc | tcacacctgc | aggccacggc | gccgctgctg | 900 |
| cacccactc | agacccgca | ccgcatcac | caccaccacc | atcacggcgg | cggggcgcc | 960 |
| ccggtgagcg | cggggacgat | tttctaaccc | cagggagaac | tcgccagaga | ctgagagcag | 1020 |
| agaccactta | tcctcattgc | ttaccccgag | ccggggttcc | ctcctcccgg | cccgctgccg | 1080 |
| ccacccacct | ctcctgcagg | ctgcgacctg | cagtggcccg | tctcaggccc | tgctcactcc | 1140 |
| cggggccacc | aaacgggccc | ctctctcggg | ggaaccggac | agcagcttgg | caaaggcctc | 1200 |
| cctaaaaggc | cgcatttctg | acctgagccc | cgggtctcgg | ctgtttcgag | ccccgcctcg | 1260 |
| gacttgcctt | ccctccccctc | cggtgagcc | tgtctggcgc | cttcctcgcc | ccgggctgag | 1320 |
| agctgggtcc | cgggagatgg | aagcctccca | ggcgcgcgag | gcttccgggg | cgctctgagg | 1380 |
| cttctttctc | ctcgcccgct | cccctgggct | cagctcggac | gctgcagtta | ttgacctccc | 1440 |
| ggtcccgcct | gcccgccctc | ccccacgtgg | cccttgacc | cgggcggccc | cgccgcttct | 1500 |
| ttccttcctg | cagttcccag | ccctcggagc | ccccatccct | tatcttaccc | ccaccgcgct | 1560 |
| cccccaggag | cgctcccctca | gctctctcct | catccatcac | cagtggagtt | tttttatttt | 1620 |
| ttatttttt | aaaagtttag | gtgcctttgc | ggatgacctc | attttgacgt | tgaaaaaatg | 1680 |
| atttttaat | atgtgaacac | tgcaaaaatg | tgtttaaatt | atcttttta | aaacctattc | 1740 |
| aggattatta | gcctggactt | ggacacagag | tttgtaaata | aaggtgtctg | tgcagatttt | 1800 |
| cccactgatt | tatttgtata | aaaatactca | tcttttcaga | ctttttgta | aaccccagt | 1860 |
| tgtgaaaact | gcagtttagc | agtgacctca | gcaacccctc | ctttttattt | tttccttttaa | 1920 |
| aaacatttca | gttaaattaa | gctactgatt | tggatttgtt | ttatcgtatc | ctaaagtctt | 1980 |
| tgttgttgaa | atgaaaggta | ttttgggggtt | atttattatg | aaaacaacat | gctcttaatg | 2040 | ttgattttac aatatgaaga gattatttaa ataaattatt gttttcattg g    2091

<210> SEQ ID NO 2
<211> LENGTH: 328
<212> TYPE: PRT
<213> ORGANISM: Homo sapiens

<400> SEQUENCE: 2

Met Thr Gly Val Phe Asp Ser Leu Val Ala Asp Met His Ser Thr Gln
 1               5                  10                  15

Ile Ala Ala Ser Ser Thr Tyr His Gln His Gln Pro Pro Ser Gly
            20                  25                  30

Gly Gly Ala Gly Pro Gly Gly Asn Ser Ser Ser Ser Ser Leu His
        35                  40                  45

Lys Pro Gln Glu Ser Pro Thr Leu Pro Val Ser Thr Ala Thr Asp Ser
 50                  55                  60

Ser Tyr Tyr Thr Asn Gln Gln His Pro Ala Gly Gly Gly Gly Gly
 65              70                  75                  80

Gly Ser Pro Tyr Ala His Met Gly Ser Tyr Gln Tyr Gln Ala Ser Gly
                85                  90                  95

Leu Asn Asn Val Pro Tyr Ser Ala Lys Ser Ser Tyr Asp Leu Gly Tyr
            100                 105                 110

Thr Ala Ala Tyr Thr Ser Tyr Ala Pro Tyr Gly Thr Ser Ser Ser Pro
        115                 120                 125

Ala Asn Asn Glu Pro Glu Lys Glu Asp Leu Glu Pro Glu Ile Arg Ile
    130                 135                 140

Val Asn Gly Lys Pro Lys Lys Val Arg Lys Pro Arg Thr Ile Tyr Ser
145                 150                 155                 160

Ser Phe Gln Leu Ala Ala Leu Gln Arg Arg Phe Gln Lys Thr Gln Tyr
                165                 170                 175

Leu Ala Leu Pro Glu Arg Ala Glu Leu Ala Ala Ser Leu Gly Leu Thr
            180                 185                 190

Gln Thr Gln Val Lys Ile Trp Phe Gln Asn Arg Arg Ser Lys Phe Lys
        195                 200                 205

Lys Met Trp Lys Ser Gly Glu Ile Pro Ser Glu Gln His Pro Gly Ala
    210                 215                 220

Ser Ala Ser Pro Pro Cys Ala Ser Pro Pro Val Ser Ala Pro Ala Ser
225                 230                 235                 240

Trp Asp Phe Gly Val Pro Gln Arg Met Ala Gly Gly Gly Pro Gly
                245                 250                 255

Ser Gly Gly Ser Gly Ala Gly Ser Ser Gly Ser Ser Pro Ser Ser Ala
            260                 265                 270

Ala Ser Ala Phe Leu Gly Asn Tyr Pro Trp Tyr His Gln Thr Ser Gly
        275                 280                 285

Ser Ala Ser His Leu Gln Ala Thr Ala Pro Leu Leu His Pro Thr Gln
    290                 295                 300

Thr Pro Gln Pro His His His His His His Gly Gly Gly Gly Ala
305                 310                 315                 320

Pro Val Ser Ala Gly Thr Ile Phe
                325

<210> SEQ ID NO 3
<211> LENGTH: 24
<212> TYPE: DNA
<213> ORGANISM: Artificial Sequence

```
<220> FEATURE:
<223> OTHER INFORMATION: sense primer corresponding to part of mouse
GAD67

<400> SEQUENCE: 3
aaggcatggc ggctgtgccc aaac                                            24

<210> SEQ ID NO 4
<211> LENGTH: 24
<212> TYPE: DNA
<213> ORGANISM: Artificial Sequence
<220> FEATURE:
<223> OTHER INFORMATION: antisense primer correspond to part of mouse
GAD67

<400> SEQUENCE: 4
accaccccag gcagcatcca catg                                            24

<210> SEQ ID NO 5
<211> LENGTH: 23
<212> TYPE: DNA
<213> ORGANISM: Artificial Sequence
<220> FEATURE:
<223> OTHER INFORMATION: sense primer corresponding to part of mouse
Dlx2

<400> SEQUENCE: 5
ggcaccagtt cgtctccggt caa                                             23

<210> SEQ ID NO 6
<211> LENGTH: 21
<212> TYPE: DNA
<213> ORGANISM: Artificial Sequence
<220> FEATURE:
<223> OTHER INFORMATION: antisense primer corresponding to part of
mouse
      Dlx2

<400> SEQUENCE: 6
cgccgaagtc ccaggatgct g                                               21

<210> SEQ ID NO 7
<211> LENGTH: 23
<212> TYPE: DNA
<213> ORGANISM: Artificial Sequence
<220> FEATURE:
<223> OTHER INFORMATION: sense primer corresponding to part of mouse
GAPDH

<400> SEQUENCE: 7
gtggcaaagt ggagattgtt gcc                                             23

<210> SEQ ID NO 8
<211> LENGTH: 21
<212> TYPE: DNA
<213> ORGANISM: Artificial Sequence
<220> FEATURE:
<223> OTHER INFORMATION: antisense primer corresponding to part of
mouse
      GAPDH

<400> SEQUENCE: 8
gatgatgacc cgtttggctc c                                               21
```

PRODUCTION OF GABAERGIC CELLS

CROSS-REFERENCE TO RELATED APPLICATIONS

This application claims the benefit of U.S. provisional application Ser. No. 60/218,221, filed Jul. 14, 2000, which application is incorporated herein by reference in its entirety.

GOVERNMENT RIGHTS

The United States Government may have certain rights in this application pursuant to National Institute of Mental Health Grant Nos. RO1 MH49428-01, RO1 MH51561-01A1 and K02MH01046-01.

FIELD OF THE INVENTION

The invention relates generally to methods and compositions for use in production of GABAergic cells.

BACKGROUND OF THE INVENTION

The vast majority of neurons in the forebrain use either glutamate or gamma aminobutyric acid (GABA) as a neurotransmitter. Whereas glutamate sends excitatory signals, GABA sends inhibitory signals in the adult brain. In the cerebral cortex, projection neurons (neurons that project their axons to distant targets) are glutaminergic whereas local circuit neurons (interneurons) are GABAergic. Imbalances in the function of these physiologically antagonistic cell types can lead to disorders such as epilepsy, which is generally due to excessive excitatory activity. Epilepsy can be treated with medicines that mimic the function of GABAergic cells.

Unlike the cerebral cortex, most projection neurons of the basal ganglia (striatum and globus pallidus) are GABAergic. Disorders such as Huntington's disease lead to the degeneration of these neurons. Despite their large numbers and essential functions, little is known about the specification and differentiation of GABAergic neurons of the forebrain, or the precise genetic mechanisms regulating these phenomena.

One family of genes, the Dlx homeobox genes, has attracted interest due to their patterns of expression in the forebrain during development. Early in gestation, Dlx gene expression in the telencephalon is restricted to the primordia of the basal ganglia, and is excluded from the cerebral cortex (Porteus et al. (1991) *Neuron* 7:221–229; Bufone et al. (1993) *J. Neurosci.* 13(7):3155–3172), where its expression is co-extensive with cells producing GABA (Anderson et al. (1997) *Neuron* 19:27–37). Then, beginning around E12.5, Dlx+/GABA+ cells are found migrating along two tangential pathways that introduce these cells into cortical regions of the telencephalon: a lateral and a medial pathway. The lateral migratory pathway originates in both the lateral and medial ganglionic eminences of the basal ganglia and introduces specific types of Dlx+/GABAergic interneurons in the striatum, olfactory cortex, neocortex and hippocampus (Porteus et al. (1994) *J. Neurosci.* 14(11):6370–6383; Anderson et al. (1997) *Science* 278:474–476). Mice lacking Dlx1 and Dlx2 have a four-fold reduction in the numbers of GABAergic neocortical neurons (Anderson et al. (1997) *Science* 278:474–476). Others have also identified this lateral pathway, but had not demonstrated GABAergic interneurons in this pathway prior to our discovery (deCarlos et al. (1996) *J. Neurosci.* 16:6146–6156; Tamamaki et al. (1997) *J. Neurosci.* 17:8313–8323). Since then other groups have also reported migration along the lateral pathway (Lavadas et al. (1999) *J. Neurosci.* 19:7881–7888; Wichterle et al. (1999) *Nat. Neurosci.* 2:461–466.

The medial migratory pathway (also known as the rostral migratory stream), appears to originate in the region of the lateral ganglionic eminence and septum, and is the source for GABAergic interneurons of the olfactory bulb and perhaps subsets of cortical interneurons. See, Gadisseux et al. (1992) *J. Comparative Neurol.* 324:94–114; Luskin (1993) *Neuron* 11:173–189; DeDiego et al. (1994) *Eur. J. Neurosci.* 6:983–997; Lois and Alvarez-Buylla (1994) *Science* 271:264:1145–1148; and Meyer et al. (1998) *J. Comp. Neurol.* 397:493–518. This pathway contains Dlx+ cells (Porteus et al. (1994) *J. Neurosci.* 14(11):6370–6383); Dlx1 and Dlx2 mutants have a >95% reduction in the number of GABAergic neurons of the olfactory bulb (Bulfone et al. (1998) *Neuron* 21:1273–1282).

The lateral pathway, and perhaps the medial as well, seed the proliferative zone (subventricular zone) of the postnatal rodent brain with Dlx+ cells. This proliferative zone is known to be the source of postnatal neurogenesis. In particular, this proliferative zone is a source of GABAergic interneurons of the olfactory bulb (Luskin (1993) *Neuron* 11:173–189; and Lois and Alvarez-Buylla, (1994) *Science* 264:1145–1148).

The identity and relationship of the Dlx gene family members are just beginning to be elucidated. To date, six mammalian Dlx genes have been identified, of which four (Dlx1, Dlx2, Dlx5 and Dlx6) are expressed in the central nervous system (CNS). Within the CNS they appear to be exclusively expressed in the forebrain, where they are expressed in most, if not all, developing GABAergic cells. See, Porteus et al. (1991) *Neuron* 7:221–229; Price et al. (1991) *Nature* 351:748–751; Bulfone et al. (1993) *Mech. Dev.* 40(3):187; Simeone et al. (1994) *Proc. Natl. Acad. Sci. USA* 91:2250–2254; Stock et al. (1996) *Proc. Natl. Acad. Sci. USA* 93:10858–10863; Liu et al. (1997) *Dev. Dyn.* 210:498–512; Anderson et al. (1997) *Neuron* 19:27–37; Anderson et al. (1997) *Science* 278:474–476; Bulfone et al. (1998) *Neuron* 21:1273–1282; and Anderson et al. (1999) *Cereb. Cortex* 6:646–54.

Expression of the Dlx genes generally occurs in a temporal sequence during differentiation of GABAergic cells, with expression of these genes being at least somewhat overlapping. Dlx1 and Dlx2 are expressed first, in mitotically active progenitor cells within the ventricular zone; expression of Dlx1 and Dlx2 is followed by Dlx5, and finally Dlx6 (Liu et al. (1997) *Dev. Dyn.* 210:498–512). This temporal relationship implies a regulatory cascade in which the early expressing Dlx genes regulate the expression of later expressed Dlx genes.

Evidence of a Dlx regulatory cascade is supported by observations of Dlx expression in transgenic mice lacking distinct Dlx genes. For example, in the mice lacking Dlx1 and Dlx2 expression (transgenic "knock-out" mice), Dlx5 and Dlx6 expression is greatly attenuated in the forebrain (Anderson et al. (1997) *Neuron* 19:27–37). Studies with the Dlx1/Dlx2 transgenic knockout mice also indicate at least some degree of functional redundancy between the Dlx genes, further complicating the study of this complex gene family. For example, mice carrying single mutations in either Dlx1 or Dlx2 have very mild defects in their forebrain, whereas the Dlx1/Dlx2 double mutant mice have a severe block in the differentiation of basal forebrain GABAergic neurons in the basal forebrain and basal ganglia (Anderson et al. (1997) *Neuron* 19:27–37). These transgenic animal studies have supported the notion that development of GABAergic forebrain cells depends on the function of the Dlx genes: roughly 80% of neocortical, and greater than 95% of olfactory bulb and hippocampal GABAergic interneurons do not fully develop in Dlx1/Dlx2 double mutant transgenic mice (Anderson et al. (1997) *Science* 278:474–476; and Bulfone et al. (1998) *Neuron* 21:1273–1282).

Recent evidence shows that neurotransmitter subtype specification is linked to dorsoventral patterning (Marin et al. (2000) *J. Neurosci.* 20:6063–6076; and Wilson and Rubenstein, (2000) *Neuron* 28:641–651). For example, in the ventral spinal cord, longitudinal progenitor domains, that are arrayed as distinct dorsoventral tiers, give rise to distinct types of neurons: cholinergic motor neurons arise from more ventral positions than most GABAergic interneurons (Briscoe et al. (2000) *Cell* 101:435–445; and Sander et al. (2000) *Genes Dev.* 14:2134–2139). A similar organization appears to be found in the embryonic telencephalon. In both of these tissues, Nkx genes regulate specification of cholinergic neurons (Sussel et al. (1999) *Development* 126:3359–3370). Transcription factors that are expressed in progenitor domains abutting GABAergic neuronal zones are candidates for regulating GABAergic specification.

In the telencephalon, members of the Dlx homeobox gene family are expressed in, and regulate the development of the primordia of the basal ganglia (Anderson et al. (1997) *Neuron* 19:27–37). These large nuclei consist of GABAergic projection neurons. In addition, the Dlx genes are expressed in, and regulate the development of, neurons that tangentially migrate from the basal telencephalon into the cerebral cortex (Anderson et al. (1997) *Science* 278:474–476; and Pleasure et al. (2000) *Neuron* 28:727–740). These neurons give rise to GABAergic interneurons of the cerebral cortex, hippocampus and olfactory bulb (Bulfone et al. (1998) *Neuron* 21:1273–1282; and Lavdas et al. (1999) *J. Neurosci.* 19:7881–7888). The cortical GABAergic and glutamatergic neurons arise from distinct telencephalic progenitor zones and are under distinct genetic controls (Anderson et al. (1997) *Science* 278:474–476; Parnavelas, J. G. (2000) *Trends Neurosci.* 23:126–131; and Hevner et al. (2001) *Neuron* 29:353–366).

The molecular mechanisms through which the Dlx genes regulate the development of forebrain GABAergic neurons remain to be elucidated. As is evident from the above, while great strides have been made in understanding the production of GABAergic neurons, no one line of evidence has pointed to a distinct single gene or set of genes that can guide an immature cell toward development into a GABAergic cell. Without a simple, elegant system to trigger development of GABAergic neurons, there is little hope for the production of GABAergic cells in vitro in numbers that render the cells useful in, for example, screening assays to identify new drugs that regulate interneuronal activity or as sources of cells for replacement therapy. The present invention addresses this problem.

SUMMARY OF THE INVENTION

The invention features methods and compositions for the production of GABAergic cells, particularly GABAergic neurons. Production of GABAergic cells is accomplished by increasing activity of a Dlx gene (e.g., DLX1, DLX2, or DLX5) in an immature neuronal cell. The increase in Dlx activity causes differentiation of the immature neuronal cell into a neuronal cell exhibiting the GABAergic phenotype. The invention also encompasses use of GABAergic cells produced by the method of the invention in, for example, identification of agents that affect GABAergic cell activity and survival, and in replacement therapy.

BRIEF DESCRIPTION OF THE DRAWINGS

FIGS. 1A–F are photographs showing the results of immunohistochemical analysis of cortical cultures from wild type (wt) (FIGS. 1A and D) and Dlx1/2$^{-/-}$ (FIGS. 1B, C, E, and F) mouse forebrain, infected with a control virus (FIGS. 1A, B, D, E) or with a LZRS$^{pBMN-Dlx2}$ virus (FIGS. 1 C,F). FIGS. 1A–C: Dlx2 immunoreactivity; FIGS. 1D–F: Gaba immunoreactivity. Calibration bar=20 micron.

FIG. 2 is a photograph showing the results of RT-PCR analysis of GAD67, Dlx2, and GAPDH expression in wild type and Dlx1/2$^{-/-}$ cells. Lane 1: DNA ladder, 1 kb band marked. Lane 2: cDNA for GAD67, Dlx2, or GAPDG. Lane 3: wt cultures infected with a control virus. Lane 4: Dlx12$^{-/-}$ cultures infected with a control virus. Lane 5: Dlx1/2$^{-/-}$ cultures infected with LZRS$^{pBMN-Dlx2}$ virus.

FIGS. 4E and 4J are immunofluorescent labels of GAD65$^+$ and DLX$^+$ cells, respectively.

FIGS. 8A–S$_{Po}$ are a series of fluorescence images showing a 50 μm section of the Dlx expression vectors expressing Dlx5/6 enhancer/reporter construct.

DETAILED DESCRIPTION OF THE PREFERRED EMBODIMENTS

Figure 3:
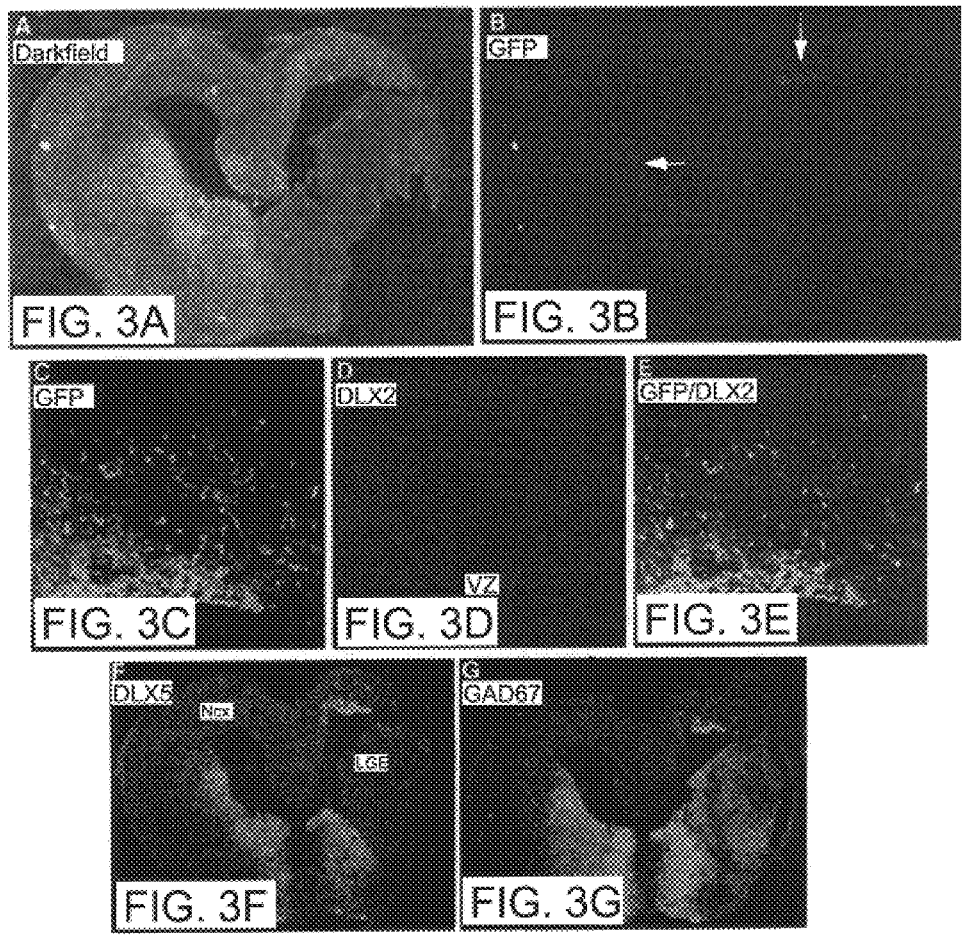
FIGS. 3A–G are photographs showing the results of electroporation of Dlx2 into cells of the cerebral cortex. Dlx5 has similar properties.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated or intervening value, in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural references unless the context clearly dictates otherwise. Thus, for example, reference to "a cell" includes a plurality of such cells and reference to "the Dlx gene" includes reference to one or more Dlx genes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided might be different from the actual publication dates, which may need to be independently confirmed.

Definitions

By "immature cell" is meant a cell that has not yet committed to a developmental pathway, and thus manipulation of the cell to provide for an increase in DLX activity in the cell, can result in maturation of the cell toward a GABA$^+$ phenotype. "Immature cells" thus include, but are not necessarily limited to embryonic stem (ES) cells, cells obtained from neural plate, cells obtained from early neutral tube, and the like.

By "Dlx activity" is meant activity of a Dlx polypeptide or biologically active fragment thereof, in regulating transcription of genes in the developmental pathway that leads to production of the GABA$^+$ phenotype. Increasing Dlx activity can be accomplished by, for example, increasing expression of one or more Dlx genes (e.g., increasing expression of Dlx1, Dlx2, Dlx5, or any combination of Dlx1, Dlx2, or Dlx5) or otherwise increasing the amount of Dlx polypeptide in the cell (e.g., by introduction of a Dlx polypeptide into the cell in a manner that facilitates an increase in Dlx transcriptional activity).

By "Dlx polypeptide" is meant a polypeptide that provides for the biological activity of a Dlx family member, e.g., facilitates transcription as does a DLX family member. Of particular interest are the DLX polypeptides DLX1, DLX2, and DLX5.

By "GABA$^+$" is meant a neuronal cell that produces and packages gamma-aminobutyric acid (GABA) in neurotransmitter vesicles.

By "GABAergic phenotype" is meant a neuronal cell that produces and packages GABA in neurotransmitter vesicles and that may, or may not also express other features of GABA+ forebrain neurons, such as glutamic acid decarboxylase (GAD; the enzyme that synthesizes GABA), the GABA vesicular transporter, and a variety of neuropeptides (e.g., enkephalin, dynorphin, substance P, NPY, somatostatin, and nitric oxidase synthase).

By "GABAergic cell" meant a neuronal cell that is capable of producing and expressing GABA in neurotransmitter vesicles.

Overview

The invention is based on the discovery that increasing Dlx activity (e.g., by increasing activity of Dlx1, Dlx2, Dlx5, or a combination thereof, e.g., due to the induction of a transcriptional cascade) in an immature neuronal cell results in production of a GABA$^+$ cell, e.g., a GABAergic neuron. Specifically, the inventors have shown that the DLX1, DLX2, or DLX5 proteins can induce cortical cells which ordinarily do not and would not exhibit a GABA$^+$ phenotype to become GABA$^+$. increasing Dlx activity in an immature neuronal cell, as well as GABAergic cells produced by the method and their use in various screening assays and in replacement therapy.

The expression of the Dlx homeobox genes is closely associated with neurons that express gamma-aminobutyric acid (GABA) in the embryonic rostral forebrain. To test whether the Dlx genes are sufficient to induce some aspects of the phenotype of GABAergic neurons, the electroporation method was used to ectopically express DLX proteins in slice cultures of the mouse embryonic cerebral cortex. This approach showed that ectopic expression of Dlx2 and Dlx5 induced the expression of glutamic acid decarboxylases (GADs), the enzymes that synthesize GABA. This method was also used to show cross-regulation between different Dlx family members. Dlx2 can induce Dlx5 expression, and Dlx1, Dlx2 and Dlx5 can induce expression from a Dlx5/6-LacZ enhancer/reporter construct.

The invention also encompasses increasing activity of transcription factors that exhibit expression patterns that are similar to the expression patterns of Dlx2 (and/or other Dlx family members), exhibit functional redundancy with Dlx1 and/or Dlx2 (e.g., are upregulated in cells that are defective for Dlx1 and/or Dlx2), and/or are expressed "upstream" of Dlx2 (and thus can induce or regulate Dlx2 expression).

Various aspects of the invention will now be described in more detail.

Source of Immature Neuronal Cells

Host cells suitable for use in the methods of the invention can be obtained from a variety of sources. These sources include, but are not necessarily limited to, naturally occurring sources, recombinantly-produced cells, cells from in vitro cultures, and the like. The host cells can be from any suitable origin, preferably mammalian, e.g., murine (mouse, rat, etc.), primate (including human), etc.

In one embodiment, the host cells are obtained from the neural plate or early neural tube of a developing embryo. To this end, two general methods can be used. The first involves using explants from the early central nervous system. Forebrain regions are preferable, but more posterior regions may also be suitable. The explants are surgically dissected from the rest of the embryo, and from other brain regions, with or without the aid of a sectioning device (e.g., vibratome). The explants are then grown in tissue culture using methods described in Anderson et al. (1997) Neuron 19:27–37; Anderson et al. (1997) Science 278:474–476; and Shimamura et al. (1997) Development 124:2709–2718.

The second method involves dissociating the explants into single cells using a titration method as used in Anderson et al. (1999) Cereb. Cortex 6:646–654. In another embodiment, the host cells are obtained from an in vitro cell culture, e.g., from a stable clone of a neural stem cell. For example, human engraftable human neural stem cells, and methods of producing such cells are described in U.S. Pat. No. 5,958,767. Mammalian neural crest stem cells and methods of obtaining the same are described in U.S. Pat. Nos. 5,589,376 and 5,824,489. Proliferated neuron progenitor cell product and methods for making same are described in U.S. Pat. No. 5,411,883.

Methods for Increasing Dlx

An increase of Dlx activity in an immature neuronal cell can be accomplished in a variety of ways. In general, increasing Dlx activity is increased by contacting an immature neuronal host cell with an agent that provides for an increase of Dlx activity in the cell (i.e., a Dlx activity-enhancing agent). Such agents include, but are not necessarily limited to, polynucleotides (e.g., DNA or RNA) encoding Dlx or a portion thereof retaining Dlx activity, Dlx polypeptides or fragments thereof retaining Dlx activity, and small molecules that cause an increase in Dlx expression or mimic Dlx activity.

It should be noted that the invention encompasses GABAergic cells produced as a direct result of contacting the immature cells with a Dlx activity-inducing agent (e.g., cells that express DLX from an introduced polynucleotide, e.g., a polynucleotide encoding DLX1, DLX2, or DLX5), as well as $GABA^+$ cells induced by factors secreted from the cells in the culture that became GABAergic as a result of the method described herein. In addition, the invention encompasses increasing Dlx expression (e.g., expression of DLX1, DLX2, DLX5, or a combination of these genes) in addition to increasing expression of other factors that can enhance development of the GABAergic phenotype (e.g., sonic hedgehog, and the like).

Specific, non-limiting examples for increasing Dlx activity in a host cell are described in more detail below.

Dlx Polynucleotides

In one embodiment, Dlx activity in the host cell is increased by contacting the host cell with a polynucleotide (e.g., DNA or RNA) that encodes a DLX polypeptide, or a fragment thereof that retains activity as a transcriptional activator. In this context, "contacting" generally means contacting with the cell the polynucleotide so as to accomplish introduction of the polynucleotide into the host cell and expression therein to produce a polypeptide that exhibits Dlx2 activity (e.g., that provides for induction of the Dlx transcriptional cascade). The introduced polynucleotide can be maintained as an episomal element, or can be chromosomally integrated. Expression of the encoded DLX polypeptide can be either chronic or transient (e.g., short-term, not for the life of the cell).

Polynucleotides encoding Dlx genes have been described and are readily available. For example, the sequence of a polynucleotide encoding a human Dlx2 is provided at GenBank accession no. NM_004405 (McGuinness et al., May 7, 1999; see also, McGuinness et al. (1996) *Genomics* 35:473–485). The sequence of a polynucleotide encoding a mouse DLX2 is provided at GenBank accession no. NM_010054 (McGuinness et al. Feb. 1, 2000, see also, McGuinness et al. (1996) *Genomics* 35:473–485). The nucleotide (SEQ ID NO:1) and amino acid sequence (SEQ ID NO:2) of the human Dlx2 is provided in the Sequence Listing. The coding sequence for human Dlx2 is provided by joining 987 . . 1386, 1878 . . 2062, and 2574 . . 2975.

Constructs and promoters suitable for delivery of Dlx polynucleotides, and methods of constructing such, are well known in the art. Likewise, introduction of a Dlx-encoding polynucleotide into the cell can be accomplished according to methods well known in the art (e.g., through use of electroporation, microinjection, lipofection, infection with a recombinant, preferably replication-deficient, virus, and other means well known in the art). Preferably, the Dlx-encoding nucleic acid is operably linked to a promoter that facilitates a desired level of DLX polypeptide expression (e.g., a promoter derived from viruses (e.g. CMV, SV40, adenovirus), or a tissue-specific or cell type-specific (e.g., beta-actin or neuronal-specific promoter). Recombinant cells containing the Dlx-encoding nucleic acid can be selected and/or enriched via, for example, expression of a selectable marker gene present in the Dlx-encoding construct or that is present on a plasmid that is co-transfected with the Dlx-encoding construct. Typically selectable markers provide for resistance to antibiotics such as tetracycline, hygromycin, neomycin, and the like. Other markers can include thymidine kinase and the like.

In one embodiment, Dlx expression is transient, e.g., is provided for a period of time that is not permanent. In general, this can be accomplished by using a construct that remains episomal (e.g., does not become genomically integrated to any significant degree) or by providing for regulated expression that requires an exogenous regulatory factor to induce expression (e.g., detectable or significant expression occurs only the presence of the exogenous factor).

DLX Polypeptides

In another embodiment, Dlx activity is enhanced in the cell by introducing a DLX polypeptide (e.g., DLX1, DLX2, DLX5), or a biologically active fragment thereof retaining DLX activity (e.g., transcriptional activity), into the immature neuronal cell. Introduction of a DLX polypeptide can be accomplished according to methods well known in the art, e.g., microinjection, delivery using lipofection (e.g., liposomes), and the like. In one embodiment, DLX polypeptide is delivered using the Voyager system (InVitrogen).

Other Agents that Enhance Dlx Activity in a Cell

Other agents that provide for enhanced DLX activity in the cell can be readily identified and used in the methods of the invention to produce GABAergic cells. The term "DLX activity-enhancing agent" as used herein describes any molecule with the capability of enhancing or mimicking the physiological function of at least one DLX gene (e.g., DLX1, DLX2, DLX5). Such agents can include other endogenous transcription factors that induce expression of Dlx, synthetic molecules (e.g., small molecule drugs, peptides, or other synthetically produced molecules or compounds, as well as recombinantly produced gene products) as well as naturally occurring compounds (e.g., polypeptides, endogenous factors present in neuronal cells, hormones, plant extracts, and the like). For example, several secreted proteins can induce Dlx expression, including sonic hedgehog (Kohtz et al. (1998) *Development* 125:5079–5089); FGFs (Ferrari et al. (1999) *Developmental Dynamics* 216(1):10–15) and BMPs.

As is evident from the above, DLX activity enhancing agents encompass numerous chemical classes. Where the agents are synthetically produced, the agents are typically organic molecules, preferably small organic compounds having a molecular weight of more than 50 and less than about 2,500 daltons. Candidate agents comprise functional groups necessary for structural interaction with proteins or nucleic acid, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A wide variety of in vitro assays can be used to identify DLX activity enhancing agents, including labeled in vitro protein-protein binding assays, protein-DNA binding assays, electrophoretic mobility shift assays, immunoassays for protein binding, and the like. The screening assay can be a binding assay, wherein one or more of the molecules may be joined to a label, and the label directly or indirectly provides a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures. The purified DLX protein may also be used for determination of three-dimensional crystal structure, which can be used for modeling intermolecular interactions, transcriptional regulation, etc.

A variety of other reagents may be included in the screening assays described herein. Where the assay is a binding assay, these include reagents like salts, neutral proteins, e.g., albumin, detergents, etc. that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hours will be sufficient.

Other assays of interest detect agents that mimic Dlx function. For example, candidate agents are added to a cell that lacks functional Dlx, and screened for the ability to reproduce Dlx activity in a functional assay.

Isolation and Identification of GABAergic Cells

GABAergic cells are identified and, where desirable, isolated away from GABAergic negative cells to provide for a substantially homogenous population of GABAergic cells. As used herein, the term "isolated" is meant to indicate that the GABAergic cell is in an environment different from that in which the progenitor cell or GABAergic cell naturally occurs. "Isolated" is meant to include populations that are substantially enriched for the cell of interest and/or in which the cell of interest is partially or substantially purified. As used herein, the term "substantially purified" refers to a cell or molecule (e.g., a polynucleotide or a polypeptide) that is removed from its natural environment and is at least 60% free, preferably 75% free, and most preferably 90% free from other components with which it is naturally associated.

The development of the $GABA^+$ phenotype can be confirmed according to any of a variety of methods. For example, GABAergic cells produced by the method of the invention can be identified by contacting the cells with an anti-GABA antibody. Alternative methods for characterizing the properties of the GABAergic cells include assays for molecules expressed in GABAergic cells using immunohistochemistry, in situ hybridization, northern blots, or western blots. Markers for GABAergic cells include: Dlx1, Dlx5, Dlx6, Glutamic acid decarboxylase, calbinidin, neuropeptide Y, nitric oxide synthase, somatostatin, Lhx6, and NPAS1. To verify that the cells do not have properties of forebrain glutaminergic cells, markers of glutaminergic cells can be assayed using the same methods. Such markers include glutamate and Tbr1 (Bulfone et al. (1998) *Neuron* 21:1273–1282).

Uses of GABAergic Cells Produced by the Methods of the Invention

The GABAergic neuronal cells produced by the methods of the invention can be used in a variety of applications both in vitro and in vivo. Examples of such uses are described below.

Screening Assays

In one embodiment, the GABAergic neuronal cells can be used in screening assays to identify agents that modulate an activity of such cells. In general, such screening assays involve contacting a candidate agent with a GABAergic cell produced according to the invention, and detecting an alteration in the an activity or phenotype of interest. Applications of this approach would include, but are not necessarily limited to, assays to identify: (1) agents that increase or decrease the response of GABAergic cells to neurotoxic agents; including the Huntington protein; (2) agents that alter the physiological properties of GABAergic cells (e.g., the expression of neurotransmitter/modulator receptors or pumps, ion channels, signal transduction machinery); (3) agents that alter the growth and/or branching of the axon or dendrites of GABAergic cells; and/or (4) agents that alter the interactions of GABAergic cells with other neurons (e.g., glutaminergic).

Reagents to Facilitate Research

In another embodiment, the GABAergic cells produced according to the invention are extremely useful as reagents. For example, GABAergic cells of the invention can be used at the bench to study, for example, the effect of various endogenous or exogenous factors upon activity of GABAergic cells and/or to further understand molecular pathways active in GABAergic cells. This utility is of paramount importance give the difficulty in obtaining specific types of neuronal cells for study, particularly where the experiments require a homogenous population of GABAergic cells or require large numbers of cells.

In addition, the GABAergic cells as well as the Dlx family of transcription factors, can be used to facilitate identification of other molecules required for GABAergic neuronal development, function and survival. This can be accomplished by, for example, using polynucleotide arrays and other methods (e.g., subtractive hybridization) to identify genes that are regulated by Dlx, e.g., exhibit increased expression upon contacting a GABAergic cell with one of these transcriptional factors or other activity-enhancing agent. This can be accomplished by, for example, comparing gene expression profiles in wild-type and mutant transgenic mice, and/or by comparing gene expression profiles in neuroepithelial stem cells that are express differing levels of Dlx.

Transplantation

In another embodiment, the GABAergic cells produced according to the invention can be used in ex vivo replacement or supplemental therapy in subjects having a condition or disease caused by or associated with a defect in GABAergic neurons. Exemplary conditions or diseases for which supplemental or replacement therapy can be useful include, but are not necessarily limited to, epilepsies, neuropsychiatric disorders (e.g., schizophrenia), Huntington's disease, and Alzheimer's disease.

In one embodiment, the GABAergic cell is derived from a donor of the same species as the recipient, more preferably from a donor having a compatible complement of MHC molecules. Where possible, it may be preferred to produce GABAergic cells from the individual who will receive the transplant (e.g., to provide an autologous transplant). For example, stem cells may be obtained from the individual's subependymal zone.

In general, after production according to the invention, the GABAergic cells are expanded in vitro, and are implanted into the subject by methods well known in the art. The number of cells implanted is a number of cells sufficient to provide for the adequate repair of the neuronal defect or deficiency. The number cells to be transplanted can be determined based upon such factors as severity of the defect in the subject and/or the percentage of cells that survive implantation. Preferably the cells are implanted in an area of dense vascularization, and in a manner that minimizes evidence of surgery in the subject. There is evidence that immature forebrain interneurons are capable of widespread migration within the cerebral cortex (Wichterle et al. (1999) Nat. Neurosci. 2:461–466; and Anderson et al. (1997) Science 278:474–476), indicating that transplants of such cells disperse throughout the recipient's cerebral cortex. The engraftment of the cells can be monitored using standard CNS imaging methods (e.g., MRI) and by examining the subject for classic signs of graft rejection, i.e., inflammation and/or exfoliation at the site of implantation, and fever. Migrating immature interneurons are likely postmitotic, and thus would not pose a risk if treatment is continued.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

The materials and methods described below are those used in the examples that follow. These materials and methods are meant to be exemplary, and not limiting as to the materials and methods encompassed by the present invention.

Virus Production

The LZRSpBMN (Kinsella and Nolan, 1996) vector was used to generate a replication incompetent retrovirus encoding full-length mouse DLX2 protein ($LZRS^{pBMN-Dlx2}$). An EcoRI-NotI fragment, encoding amino acids 1–332 of mouse Dlx2 was cloned into the corresponding sites of $LZRS^{pBMN}$. The retroviral vector $LZRS^{pBMN-LacZ}$ encoding for E. coli β-galactosidase was used to produce control virus. Titers of approximately $10^5$–$10^6$ gene transducing units/ml were obtained 48 hrs after calcium phosphate mediated transfection into Phoenix ecotropic producer cells (Grignani et al. (1998)). Cells infected with the $LZRS^{pBMN-LacZ}$ virus were assayed using X-gal immunohistochemistry. Cells infected with the $LZRS^{pBMN-Dlx2}$ virus were assayed using anti-DLX2 immunohistochemistry (Porteus et al. (1994) J. Neurosci. 44:6370–6383).

Ectopic Expression in Vitro

The effects of retrovirally driven expression of Dlx2 were studied in primary cultures of cortex derived from $Dlx1/2^{-/-}$ E15.5 embryos and their wild-type (wt) littermates. Briefly, embryos resulting from mating between $Dlx1/2^{-/-}$ heterozygous parents were examined for the presence of cleft palate (which is 100% penetrant in $Dlx1/2^{-/-}$ mice; Qiu et al. (1997)). The genotype of each embryo was then confirmed using PCR amplification of genomic DNA as described previously (Anderson et al. (1997) Neuron 19:27–37). Each brain was processed separately, the pial membrane was removed and neocortical regions corresponding to the presumptive motor and somatosensory cortex were dissected out. Cells were dissociated in 0.01% trypsin and plated on polyornithin/fibronectin coated coverslips at a density of $2 \times 10^5$ cells/ml. Two hours after plating, cells were infected with 100 μl of retroviral suspension, containing approximately $10^4$ infectious viral particles. Cells were cultured for 5 days in neurobasal medium (Gibco) containing 10 ng/ml recombinant bFGF.

Sister cultures from wild-type and $Dlx1/2^{-/-}$ cortices that were infected with a control virus or with $LZRS^{pBMN-Dlx2}$ virus were analyzed for: cell proliferation, neuronal differentiation and GABA expression. The number of proliferating cells was evaluated following exposure to $10^{-5}$ M during the last 12 hours in vitro as previously described (Cavanagh et al. (1997) Cerebral Cortex 7:293–302). Differentiating neurons identified by their immunoreactivity with a mouse monoclonal Map2 antiserum (diluted 1:500; Boehringer). GABA expressing cells were revealed using a rabbit polyclonal antiserum (diluted 1:2000; Sigma). The results represent the mean percentage ±S.E.M. of positive cells from three different experiments, in which two coverslips per experimental condition and staining procedure were evaluated. A minimum of 500 cells per coverslipped culture was counted.

RT-PCR

A minimum of $5 \times 10^4$ wild-type or $Dlx1/2^{-/-}$ cells infected with the LacZ or the Dlx2 retrovirus was harvested in 0.5 ml Triazol (Gibco). Total RNA was extracted following the manufacturer's instructions. The RNA was electrophoresed on a 1.5% agarose gel to assay for degradation. For each RT-PCR reaction, 200 ng of RNA was reverse transcribed using 2 units of AMV-RT (Promega) in the presence of 8 units of RNAse inhibitor, 5 nmoles of dNTPs and 10 pmoles of one of the following sets of primers:

mouse GAD67:

```
(sense):
AAGGCATGGCGGCTGTGCCCAAAC    (SEQ ID NO: 3)

(antisense):
ACCACCCCAGGCAGCATCCACATG    (SEQ ID NO: 4),
``` corresponding to nucleotides 817–841 (sense) and nucleotides 1108–1131 (antisense) of a GAD67 cDNA; GenBank accession number Y12257.

mouse Dlx2

```
(sense):
GGCACCAGTTCGTCTCCGGTCAA     (SEQ ID NO: 5)

(antisense):
CGCCGAAGTCCCAGGATGCTG       (SEQ ID NO: 6),
``` corresponding to nucleotides 2985–3007 (sense) and nucleotides 4205–4225 (antisense) of genomic Dlx2; GenBank accession number U51002.

mouse GAPDH

```
(sense):
GTGGCAAAGTGGAGATTGTTGCC     (SEQ ID NO: 7)

(antisense):
GATGATGACCCGTTTGGCTCC       (SEQ ID NO: 8),
``` corresponding to nucleotides 114–136 (sense) and nucleotides 382–404 (antisense) of GAPDH cDNA; GenBank accession number M32599.

Reverse transcription was carried out at 42° C. for 45 min. After adding 1 unit of Taq polymerase (Perkin-Elmer-Cetus, Emeryville, Calif.) mixtures were subjected to the following thermal cycles: 97° C. for 2 min, 1 cycle; 97° C. for 1 min, 60° C. for 1 min, 72° C. for 45 sec, 20 cycles for GADPH; 25 cycles for Dlx2 and 30 cycles for GAD67. As a positive control, a PCR reaction was carried out with 10 ng of Dlx2, GAPDH or GAD67 cDNAs as templates. Different amounts (1 µg, 500 ng, 250 ng and 125 ng) of total RNA extracted from E15.5 mouse forebrain were used as an indication that the amount of DNA amplified was a function of the starting amount of RNA. Twenty microliters of each individual PCR reaction were electrophoresed on a 1.5% agarose gel; the DNA fragments were stained with ethidium bromide. The predicted sizes of the PCR products were: 314 bp (GAD67); 365 bp (Dlx2); 280 bp (GAPDH). Genomic DNA amplification, which sometimes occurs because of contamination, could be easily differentiated from cDNA amplification by the size of the PCR products. In fact, for each primer pair, the sense and antisense primers were positioned on two different exons. In addition, no PCR amplification was obtained when AMV-RT was omitted from the reaction.

Expression Vectors

Coding regions of mouse Dlx1, Dlx2 and Dlx5 genes (Eisenstat et al. (1999) *J. Comp. Neurol.* 414:217–237; and Zerucha et al. (2000)*J. Neurosci.* 20:709–721) were cloned into pCAGGS, a chicken beta-actin-promoter driven expression vector (Niwa et al. (1991) *Gene* 108:193–199). The original vector was modified to include a greater number of restriction sites 3' of the promoter (plasmids pCAGGS/ES and pCAGGS/SE). The genes for Dlx2 and Dlx5 consisted of their complete and unmodified coding sequences, whereas that for Dlx1 lacked coding sequence for the two C-terminal amino acids and, potentially, for 5 amino acids (MTMTT) at the predicted N-terminus, which contains three closely spaced methionines. Untranslated gene sequences were kept as short as feasible, ranging from 0–7 bases at the 5'-end to maximally 8 bases at the 3'-end.

Telencephalic Slices

Preparation and maintenance of slice tissue cultures were as described in Anderson et al. (1997) *Neuron* 19:27–37.

Electroporation

A tissue slice, with its supporting membrane, was placed onto an agarose block within a setup of two horizontally oriented platinum electrodes (System CUY-700–1 and CUY-700–2; Protech International Inc., San Antonio, Tex.). A tiny agarose column (punched with a clipped hypodermic needle from a 1% agarose gel) was attached to the mobile upper electrode, a small amount of plasmid solution applied to its lower end and the electrode lowered to let the solution contact the tissue. The diameter of the column (0.5–0.8 mm) largely determined the area of the slice, which would be subjected to electroporation. The system was powered by a T820 Electro Square Porator (BTX). It was determined that plasmid concentrations of about 1 µg/µl at charging voltages of >100 V (with two pulses of 5 ms each) yielded acceptable numbers of electroporated cells.

Fixation and Re-sectioning of Slices

After incubation for up to 48 h, slices were fixed in 4% paraformaldehyde/PBS, washed in PBS and either embedded in Tissue-Tek or 5% low gelling temperature agarose/PBS for further sectioning on a cryostat (10 µm) or a vibrating blade microtome (50 µm), respectively. This material was subjected to standard in situ-hybridization and/or immunohistochemistry procedures.

In situ Hybridization

In situ hybridization was performed as described in Porteus et al. (1992) *Mol. Brain Res.* 12:7–22.

Immunohistochemistry

Immunohistochemistry was performed on 50 µm freefloating sections. Following pre-incubation for 2 h in a solution of 2% normal goat serum in PBST (PBS with 0.1% Triton X-100) and 0.1% NaN$_3$, the liquid was changed for a fresh aliquot containing the primary antibody, and the tissue incubated for up to 48 h at 4° C. Sections were subsequently washed 3× in PBST and the secondary antibody (1:200 goat anti-rabbit IgG, conjugated to either the red fluorescent dye Alexa594 (Molecular Probes), or biotin (Vector)) applied, and incubated for 4 h at RT. The biotinylated antibody was visualized with the ABC-kit (Vector), according to the manufacturers instructions. The following primary antibodies were used: anti-distal-less (rabbit polyclonal, 1:400; from Dr G. Panganiban, University of Wisconsin-Madison); anti-GAD65 (rabbit polyclonal, 1:2000; Chemicon AB5082); and anti-β-galactosidase (rabbit polyclonal, 1:2000; 5prime-3prime).

Example 1

Infection with Recombinant Retroviruses Encoding Dlx2 Leads to DLX2 Expression in Cortical Cells Derived from Dlx1/2 Mutants Neocortical primary cultures from E15.5 wild-type and Dlx1/2$^{-/-}$ mice appeared indistinguishable in morphology and density. Cells were infected with recombinant retroviruses within 2 hours of being placed in culture and grown for five days. Infection with either the LZRS$p^{BMN\text{-}LacZ}$ or LZRS$p^{BMN\text{-}Dlx2}$ virus, did not affect the growth or survival of the cells. DLX2 immunoreactive cells were readily detected in non-infected or LZRSp$^{BMN\text{-}LacZ}$ virus-infected wild-type cortical cultures (roughly 20% of the cells were DLX2 positive; FIG. 1A). Cultures derived from Dlx1/2$^{-/-}$ cortices had no DLX2-immunoreactive cells whether or not they were infected with LZRSp$^{BMN\text{-}LacZ}$ (FIG. 1B).

However, upon infection with LZRSp$^{BMN\text{-}Dlx2}$, DLX2 immunoreactive cells were found in the Dlx1/2$^{-/-}$ cultures (roughly 5% of the cells; FIG. 1C). These DLX2-expressing cells were often observed in clusters of 2–8 cells.

Example 2

Effects of Ectopic Dlx2 Expression on Proliferation, Differentiation and GABA Expression in Wild-Type and Dlx1/2$^{-/-}$ Cortical Cells The number of proliferating cells in cortical cultures derived from wild type and Dlx1/2$^{-/-}$ mice was estimated based upon the number of BrdU$^+$ cells after a 12 hr exposure to the thymidine analogue. Approximately 73±13% cells were labeled with BrdU in Dlx1/2$^{-/-}$ cultures, as compared to 76±8% in cultures from wild-type littermates. Infection of Dlx1/2$^{-/-}$ cultures with LZRSp$^{BMN\text{-}Dlx2}$ did not affect the percentage of proliferating cells (72±8%).

Next the effect of infection with LZRSp$^{BMN\text{-}Dlx2}$ on differentiation (based on expression of the neuronal marker, MAP2) was tested in the wild type and Dlx1/2$^{-/-}$ mutant neocortical cultures. No significant difference was detected in MAP2 between various cultures (34±6% of the cells were MAP2 immunoreactive in each case). While this general marker of cortical differentiation was not affected by the Dlx1/2$^{-/-}$ mutation, there was a marked reduction of GABA$^+$ cells in cortical cultures from Dlx1/2$^{-/-}$ mice (FIG. 1B) compared to cultures from wild-type mice (FIG. 1D). Specifically, 19±5% of the wild type cortical cells were GABA$^+$, whereas only 2±2% cells were GABA$^+$ in Dlx1/2$^{-/-}$ cortical cells. Upon infection with LZRSp$^{BMN\text{-}Dlx2}$, the number of GABA$^+$ cells in Dlx1/2$^{-/-}$ cultures increased roughly five-fold, to 11±3% (FIG. 1F).

Example 3

PCR Confirmation of Induction of Dlx2 and GAD Expression

The induction of Dlx2 and GAD expression via infection with the LZRSp$^{BMN\text{-}Dlx2}$ virus was assayed by RT-PCR. PCR with primers specific for GAD67 and Dlx2 generated DNA fragments of the expected size from wild-type (FIG. 2, lane 3), but no PCR products from Dlx1/2$^{-/-}$ cortical cultures (FIG. 2, lane 4). Upon infection of Dlx1/2$^{-/-}$ cortical cultures with LZRSp$^{BMN\text{-}Dlx2}$, expression of both Dlx2 (FIG. 2, lane 5), and GAD67 (FIG. 2, lane 5) RNA was confirmed.

Example 4

Confirmation of Role of Dlx2 in Vivo Using Electroporation of Brain Slices

In order to confirm the role of Dlx2 in the development of GABAergic cells, the Dlx2 construct was introduced into brain slices from Dlx1/2$^{-/-}$ mutant mice. Electroporation of forebrain slices was accomplished as described below.

Preparation of Tissue

Embryos were dissected in cold Krebs buffer. While removing the brains of early embryos, particular care was taken that the ventral side (hypothalamus) remained as intact as possible so as to improve the coherence of the slices in later steps. Tissue was kept on ice until needed. The 10×Krebs buffer stock solution was prepared according to the following formula:

| 11 | 0.51 | | |
|---|---|---|---|
| 73.6 g | 36.8 g | NaCl | 1.26 M |
| 1.87 g | 0.935 g | KCl | 25 mM |
| 1.66 g | 0.83 g | NaH$_2$PO$_4$ × H$_2$O (or 1.44 g/0.72 g anhydr.) | 12 mM |
| 2.44 g | 1.22 g | MgCl$_2$ × 6H$_2$O | 12 mM |
| 3.68 g | 1.84 g | CaCl$_2$ × 2H$_2$O | 25 mM |

0.511×Krebs buffer for slices was prepared as follows: 50 mls stock solution diluted with cold sterile H$_2$O, 1 g glucose (dextrose) and 1.05 g NaHCO$_3$ added. The solution was sterile filtered. The pH after filtration should be about 7.5–7.6.

Sterile Krebs for the slices: was prepared by adding to 50 ml of the above-filtered buffer: 0.5 ml 1M HEPES; 0.5 ml PenStrep; 100 μl 50 mg/ml gentamycin.

Sectioning

A 5% low-melting point agarose was prepared in 1×PBS and kept at 42° C. The brains were embedded by placing agarose into a tissue embedding mold, transferring the brain with as little buffer as possible, and gently stirring with a glass rod so that the agarose can properly contact the tissue. Care was taken not to tear or squeeze the brain (especially in E14.5 and younger embryos). The preparation was kept on ice until the agarose solidified, then the edges were trimmed away so that a small block suitable for sectioning is obtained. The block(s) were glued onto a mount, the vibratome adjusted, and sections of 200 or 250 microns cut in ice cold Krebs buffer. The slices were handled with a pair of spatulas, which provided good support to the tissue when it is transferred between dishes. The sections were then transferred into the cold Krebs buffer for slices, and after 10 minutes transferred onto a polycarbonate membrane, floating on MEM in a culture dish (Whatman Nucleopore Track-Membranes were then etched (Fisher special order number NC9656875). At this point, the slice was well supported and could be easily moved around. The slices were stored in a 37° C. incubator for two hours, or until the start of the electroporation.

The medium in which the slices were stored is as follows: 43.5 ml minimal essential medium; 5 ml fetal calf serum; 1 ml 25% glucose; and 1 ml PenStrep.

Electroporation

A BTX electroporation system (Electro Square Porator T820) was used. The machine was set to low voltage mode, charging voltage at 100–150V, delivering 1 or 2 pulses of 5 ms duration each. The electrode system was a custom made set of two solid platinum electrodes, one of which remains fixed in a glass petri dish, whereas the other can be freely moved (models CUY700-1 and CUY700-2 from Protech International, Inc., San Antonio, Tex.; www.protechinternational.com; electrodes manufactured by TR Tech Co. in Tokyo, Japan, purchased through Protech).

Clones

Genes were cloned into eukaryotic expression vectors that are expressed in neural cells (e.g., pCMV4, Andersson et al. (1989) J. Biol. Chem. 264:8222–8229). CsCl purified plasmids were used to keep the plasmid concentration above about 5 mg/ml; plasmids were initially resuspended water, and the final concentration adjusted with Krebs buffer.

A 1% agarose gel made with 1×Krebs buffer was used as a conductive buffer between the electrodes and the tissue (to prevent heat damage). A Bio-Rad Minigel system was well suited to cast a gel that is strictly planar on both sides, about 2 mm wide, and that can be kept fresh for hours in between the glass plates. A small block was cut from this gel to serve as a mount for the slice and placed on the bottom electrode. A filter with a brain slice was then placed on top of the agarose mount. A tiny column of agarose (which can be conveniently made in different diameters with a set of clipped and filed syringe needles) was attached to the top electrode, a drop of plasmid solution (0.5–1 $\mu$l) was transferred to the lower edge of this agarose column and the whole electrode is lowered, so that the DNA solution contacts the slice at the desired place. After the electroporation, the filter and slice were transferred to a culture dish containing 1 ml of Neurobasal medium and cultured at 37° C. (with daily changes of the medium). The slices were incubated in the following serum-free medium: 47.5 ml neurobasal medium; 1 ml B-27 supplement; 1 ml 25% glucose; 0.5 ml 0.2 M glutamine; and 1 ml PenStrep.

Where a GFP plasmid was introduced, protein expression was detectable after about 10 hours.

Results

FIG. 3 shows the results of introduction of DLX2 into cells of the cerebral cortex. Introduction of a Dlx2 expression vector induced these cells to express a GABAergic phenotype. The Dlx2 expression vector was electroporated into two locations in a telencephalic slice from a Dlx1/2$^{-/-}$ mouse. On the left side it was introduced into the lateral ganglionic eminence (LGE); on the right side it was introduced in the cerebral cortex. Dlx1/2$^{-/-}$ mutants had greatly reduced expression of Dlx5 expression in the LGE and the cortex, and greatly reduced expression of glutamic acid decarboxylase (GAD) and GABA in the cortex.

The Dlx2 expression vector was co-electroporated with an expression vector encoding the green fluorescent protein (GFP). Expression of GFP, which can be visualized in the living slice, indicates which cells were electroporated (FIGS. 3B, 3C, 3E). The expression of DLX2 protein from the Dlx2 expression vector was verified using anti-DLX2 immunofluorescence (see expression in the cortical ventricular zone (VZ) in FIGS. 3D and 3E). The effect of introducing DLX2 into this slice was assayed using in situ RNA hybridization to Dlx5 and GAD67, two markers of GABAergic cells. Electroporation of Dlx2 induced Dlx5 expression in the LGE and the neocortex (Ncx) (FIG. 3F). In addition, Dlx2 induced expression of GAD67 in the neocortex (FIG. 3G). Induction of GAD67 could not be assessed in the LGE, because this tissue already expresses this gene (see right LGE in FIG. 3G).

Example 5

Figure 4:
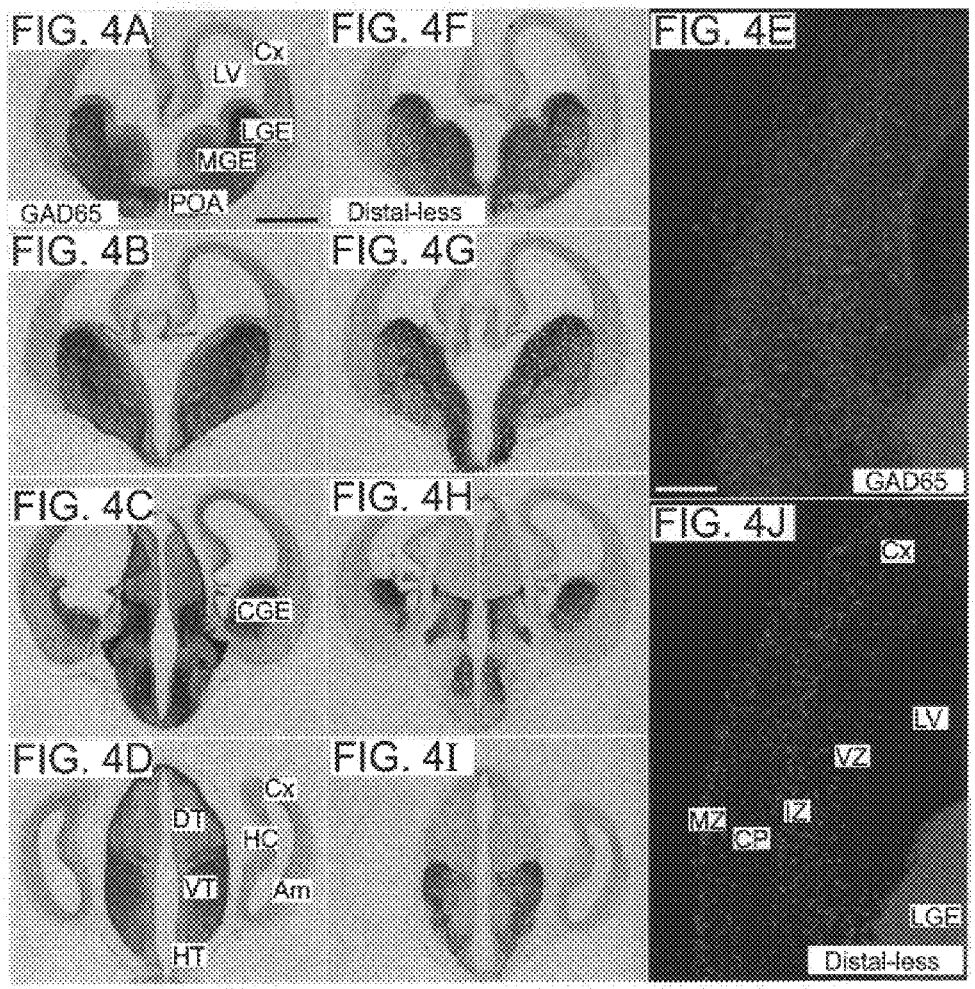
FIGS. 4A–J are a series of photographs of histochemical stain comparison of GAD65 and DLX protein expression in the forebrain of an E13.5 mouse.

Dlx2 and Dlx5, but not Dlx1, Induces Cortical Cells to Express the Glutamic Acid Decarboxylase (GAD) Genes In the embryonic forebrain, the expression pattern of the DLX family of transcription factors is nearly identical to that of the glutamic acid decarboxylases (GAD65 and GAD67), enzymes that synthesize the neurotransmitter $\gamma$-aminobutyric acid (GABA). As shown in FIG. 4, at early stages of embryonic telencephalon development, the subpallium expresses GAD65 and GAD67, and Dlx1, 2, 5, and 6, whereas the pallium does not. Once the subpallial-to-pallial tangential migration begins, which brings GABAergic cells into cortical regions, GAD65 and DLX expression show similar distributions within the cerebral cortex.

FIG. 4 is a comparison of GAD65 and DLX protein expression in the forebrain of an E13.5 mouse. Coronal sections (FIGS. 4A and F are most rostral) were histochemically stained (DAB reaction) with either an antibody to GAD65 (A–D) or Distal-less (FIGS. 4F–I), which cross-reacts with Dlx1, 2, and 5, see FIG. 5. In regions rostral to the dorsal thalamus (DT), the coincidence of GAD65 and DLX expression is striking, except for axon tracts in the hypothalamus that are only GAD65[30] (FIGS. 4C and 4D). Immunofluorescent labeling of GAD65$^+$ (FIG. 4E) and DLX$^+$ (FIG. 4J) cells shows the tangential migration from the basal telencephalon in two principal pathways into the cortex.

Abbreviations in the figure are: Am, amygdala; CGE, caudal ganglionic eminence; CP, cortical plate; Cx, cortex; DT, dorsal thalamus; HC, hippocampus; HT, hypothalamus; IZ, intermediate zone; LGE, lateral ganglionic eminence; LV, lateral ventricle; MGE, medial ganglionic eminence; MZ, marginal zone; POA, preoptic area; VT, ventral thalamus; VZ, ventricular zone. Scale bars, (a) 69 $\mu$m, (e) 14 $\mu$m.

Coincident expression of GAD65 and DLX is also notable in subdivisions of the rostral diencephalon (FIGS. 4C, 4D, 4H, and 4I). Expression of GAD posterior to the zona limitans, is not associated with DLX expression, as central nervous system expression of the Dlx genes appears to be restricted to the anterior forebrain. The spatial and temporal coincidence between DLX and GAD expression implies that the Dlx genes may have an important role in regulating GAD expression. A gain of function assay was used to test this.

Use of Electroporation of Brain Slices for Ectopic Expression of the DLX Proteins An electroporation method (Funahashi et al. (1999) Dev. Growth Differ. 41:59–72) was used to transfect Dlx expression vectors into coronal slices of the embryonic brain grown in vitro. To test whether the DLX proteins could induce GADs, the expression vectors were electroporated into the cerebral cortex from E12.5 mouse embryos. At this age, the cortex is essentially free of GAD- or DLX-positive cells, and selecting the caudal-most sections of the telencephalon for the experiments (FIGS. 4D and 4I) assured that they were severed from the subpallial sources of tangentially migrating GAD$^+$/DLX$^+$ neurons (Anderson et al. (2001) Development 128:353–363). The caudal-most sections were also consistently more efficiently electroporated.

An expression vector encoding green fluorescent protein (GFP) was co-electroporated with the Dlx expression vectors to identify the regions that expressed the transfected plasmids (FIGS. 5A, 5C, 5E, and 5G), and to assess the efficiency of each electroporation. Electroporation of Dlx1, Dlx2 and Dlx5 expression vectors led to the appearance of ectopic DLX immunoreactivity within 3 h (data not shown); by 7 h strong expression (comparable to endogenous levels) was detectable (FIG. 4B).

Figure 5:
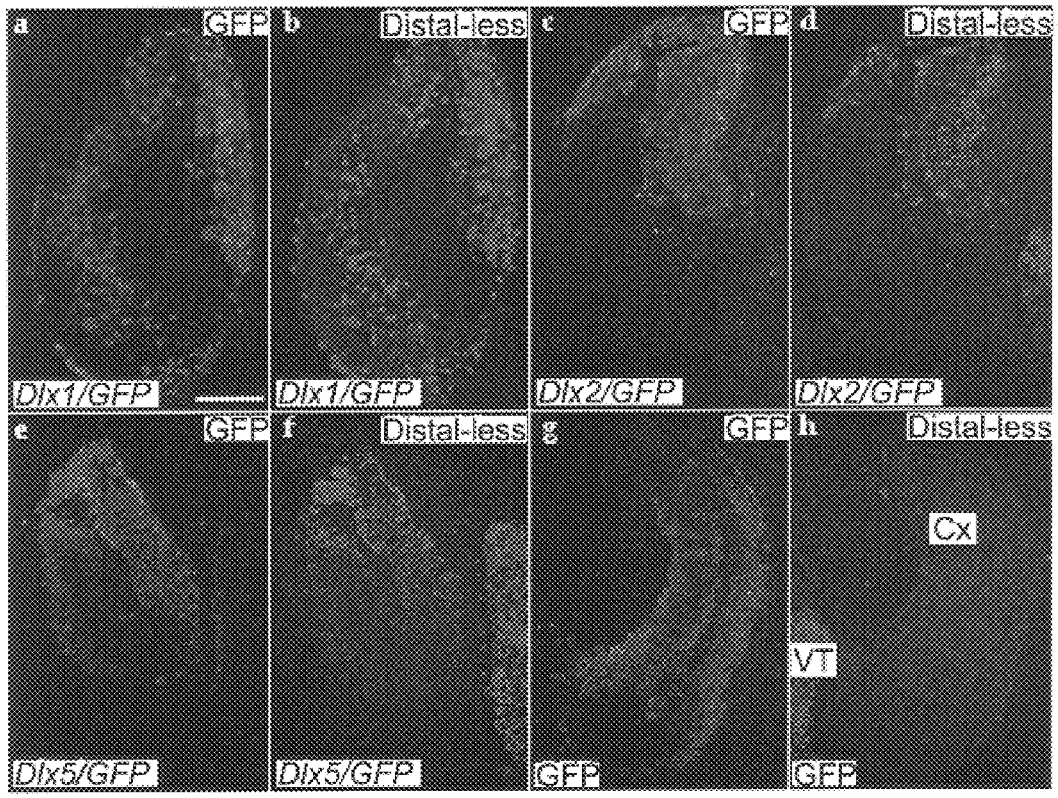
FIG. 5A–H is a series of florescence images of the same section 3 in coronal slices from caudal regions of the E12.5 mouse telencephalon. The coronal slices show electroporation of Dlx and GFP expression vectors leads to protein expression.

FIG. 5 shows that electroporation of Dlx and GFP expression vectors leads to robust protein expression in coronal slices from caudal regions of the E12.5 mouse telencephalon. Shown are pair-wise depictions of the same section in green and red fluorescence. The bottom left corner indicates which expression vectors were electroporated. GFP and DLX expression are studied in the same slice. The top right corner of each photograph indicates which protein was being analyzed: GFP expression was detected by its intrinsic green fluorescence (FIGS. 5A, 5C, 5E and 5G); DLX protein expression was detected by immunofluorescent labeling with the anti-distal-less antibody (FIGS. 5B, 5D, 5F and 5H). Electroporation of Dlx1, Dlx2 and Dlx5 all induced strong expression of the respective DLX protein in a pattern that closely resembles that of the co-electroporated GFP. Electroporation of GFP alone did not induce DLX expression (FIGS. 5G and 5H). There is also endogenous DLX expression in the VT. Abbreviations used in the figure are: Cx, cortex; and VT, ventral thalamus. Scale bar in FIG. 5A is 26 μm.

Expression from the Dlx1, Dlx2 and Dlx5 vectors produced roughly equivalent levels of DLX expression, as judged by immunofluorescence with an anti-distal-less antibody (FIGS. 5B, 5D, and 5F). The patterns of GFP and DLX expression were virtually identical (FIGS. 5A–F), suggesting extensive co-transfection of the electroporated plasmids. Counting of GFP- and DLX-positive cells showed that >95% of electroporated cells expressed both plasmids.

Ectopic Expression of Dlx Genes Induces GAD Expression

Figure 6:
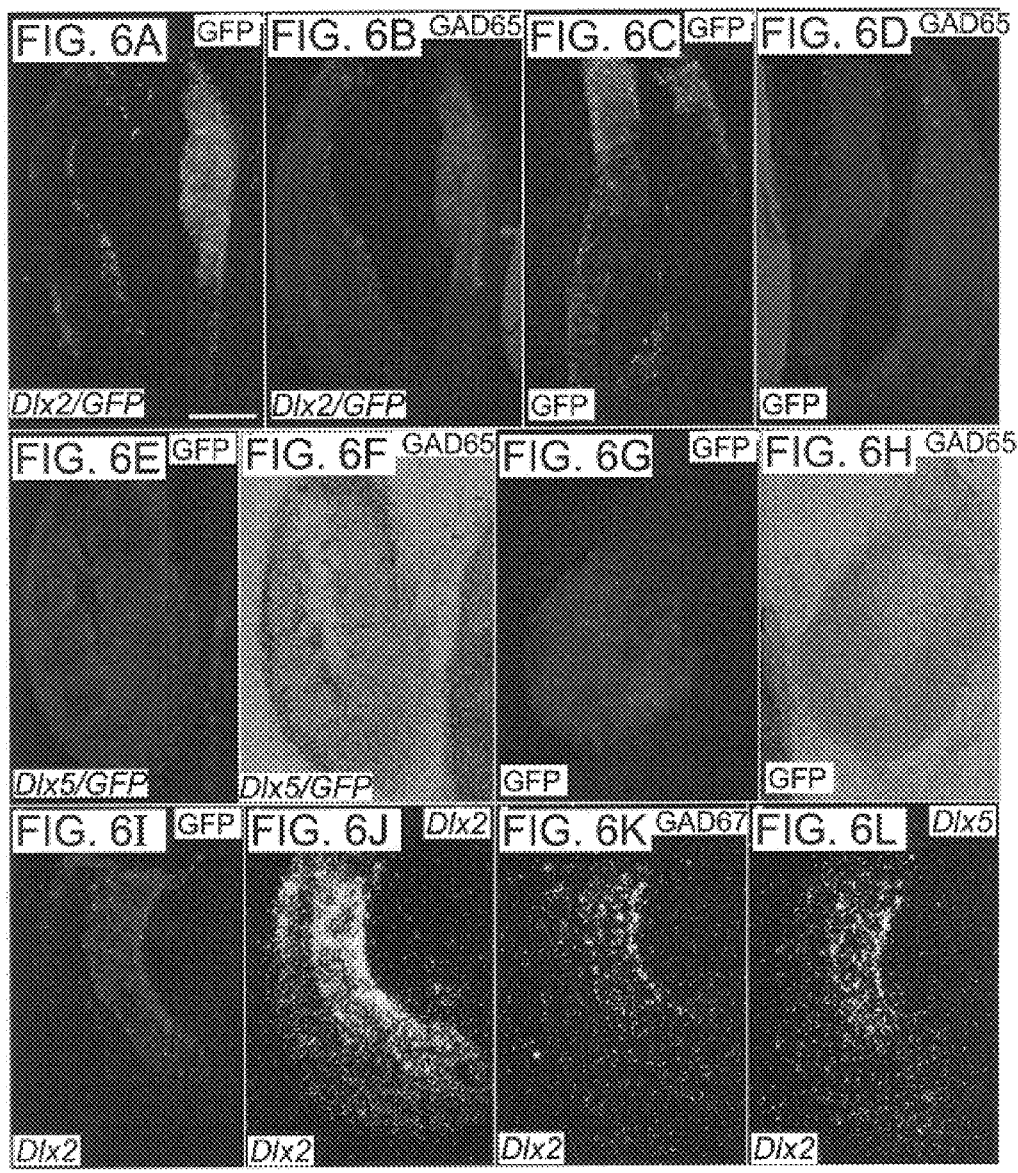
FIGS. 6A–L are a series of fluorescence images of the same section in coronal slices from caudal regions of the E12.5 mouse telencephalon. The coronal slices show electroporation of Dlx2 and Dlx5 expression vectors induces the expression of glutamic acid decarboxylases (GADs) in the caudal regions.
Figure 7:
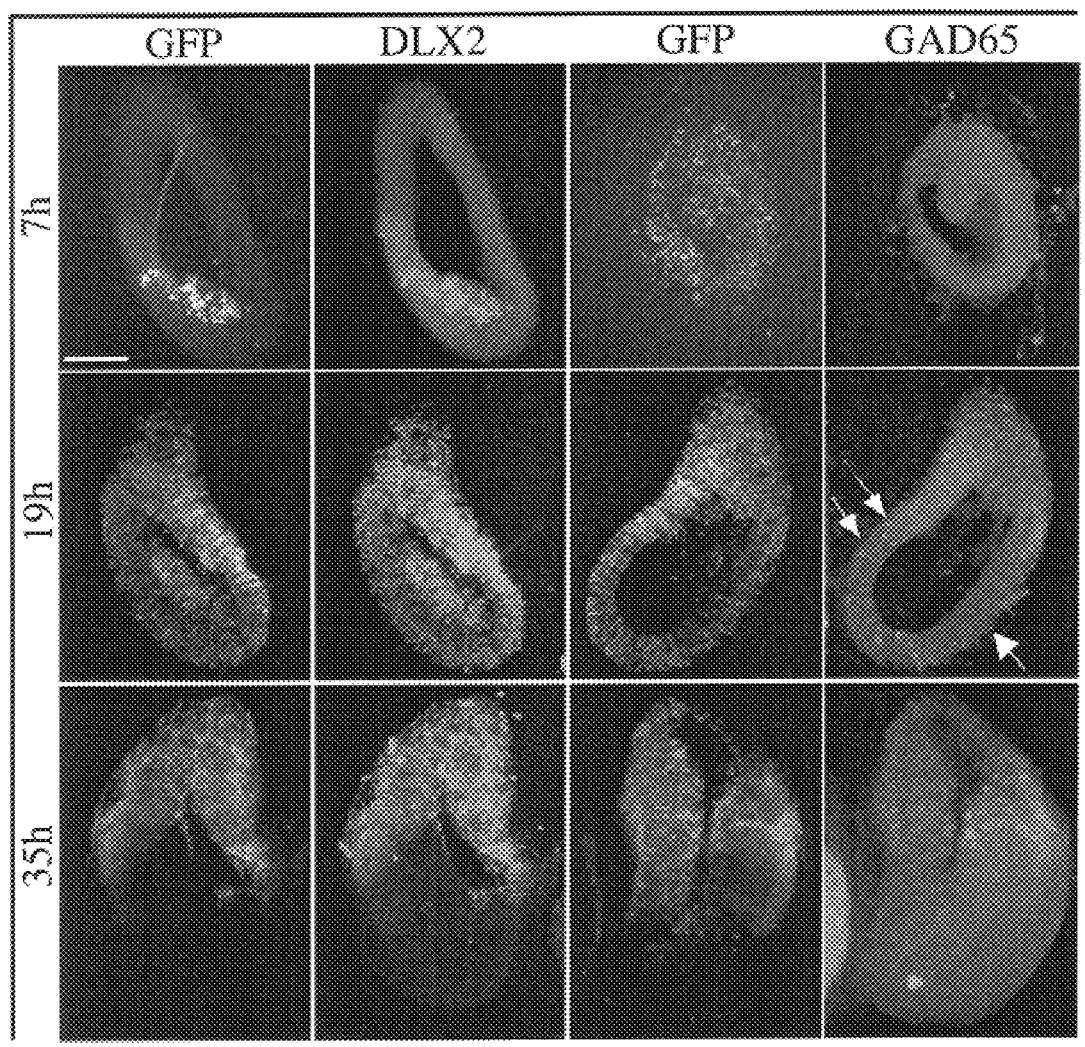
FIG. 7 is a series of photographs showing the time course of GFP, DLX, and GAD65 induction following electroporation of the Dlx2 and Gfp expression vectors. Arrows in the photograph for GAD65 at 19 hours point to cells with low levels of GAD65.

Electroporation of either the Dlx2 or Dlx5 expression plasmid readily induced GAD65 immunoreactivity (27/30 experiments for Dlx2; 12/20 for Dlx5) (FIGS. 6B, 6F, and FIG. 7). In the most effective Dlx2 electroporations, >85% of the GFP-positive cells expressed GAD65 (FIG. 6A and 6B). Dlx5 was less efficient at inducing GAD65 (FIGS. 6E and 6F), with the most effective electroporations inducing GAD65 in ~50% of the GFP-positive cells. Dlx1 was inefficient at inducing GAD65; only in 4 of 12 electroporations were any GAD65-positive cells detected, and these constituted less than 1% of the GFP-positive cells.

FIGS. 6 (A–H) shows that electroporation of Dlx2 and Dlx5 expression vectors induces the expression of glutamic acid decarboxylases (GADs) in caudal regions of the cerebral cortex of the E12.5 mouse telencephalon. Immunohistochemical detection of GAD65 protein in 50 μm free-floating sections following electroporation of Dlx2 (FIGS. 6A and 6B) or Dlx5 (FIGS. 6E and 6F). Shown are pair-wise depictions of the same section in green and red fluorescence. The control samples (FIGS. 6C and 6D) and (FIGS. 6G and 6H) represent the opposite side of the same slice, which was electroporated with the GFP plasmid alone. The bottom left corner indicates which expression vectors were electroporated. The top right corner indicates which protein was being analyzed. GFP expression was detected by its intrinsic green fluorescence (FIGS. 6A, 6C, 6E and 6G). GAD65 was visualized either by immunofluorescence (FIGS. 6B and 6D) or with the DAB reaction (FIGS. 6F and 6H).

GAD65 is robustly expressed in the majority of cells electroporated with the Dlx expression vectors (FIGS. 6B and 6F). FIGS. 6I–L show 10 μm parallel sections of a slice that was electroporated with the Dlx2 and GFP expression vectors. The top right corner indicates which protein or RNA was being analyzed. In situ hybridization with a probe for Dlx2 (FIG. 6J) confirms the abundance of RNA from the introduced plasmid in the electroporated cells when compared to the pattern for Dlx2 with that for GFP in FIG. 6I. In the same region, ectopic signals for GAD67 (FIG. 6K) and Dlx5 (FIG. 6L) are clearly detected. A probe for Dlx6 did not produce any signal (not shown). Scale bar in FIG. 6A is 26 μm.

Electroporations of binary combinations of the Dlx2 and 5 expression vectors did not appear to increase the amount of GAD65 expression compared to levels seen with the Dlx2 plasmid alone (n=3). Electroporation of the GFP expression plasmid alone never induced expression of GAD65 (n>50) (FIGS. 6C, 6D, 6G and 6H).

The kinetics of Dlx2-mediated GAD65 induction was assessed by analyzing electroporated slices after 7, 19 and 35 hours in culture (FIG. 7). Whereas strong expression of DLX2 could be detected after 7 hours, ectopic expression of GAD65 was not (n=3). GAD65 expression was detectable by 19 hours, and was increased by 35 hours (FIG. 7). FIG. 7 shows the time course of GFP, DLX and GAD65 induction following electroporation of the Dlx2 and Gfp expression vectors. Time after electroporation is shown on the left column. Electroporated slices were re-sectioned at 50 μm; distinct sections were subjected to immunohistochemistry for Distal-less protein and GAD65. Shown are pair-wise depictions of the same section in green and red fluorescence. The left column shows DLX2 immunoreactivity and the right column GAD65 immunoreactivity. Due to an experimental misfortune, the two 50 μm sections for the 7 hour time point originate from different slices. Whereas DLX2 expression is already high after 7 hours, no immunoreactivity for GAD65 is detectable at this time. GAD65 is clearly expressed by 19 hours post-electroporation, and is even more abundant after 35 hours. Arrows in the photograph for GAD65 at 19 hours point to cells with low levels of GAD65. Scale bar in FIG. 7A is 25 μm.

Electroporation of the Dlx2 vector also induced the expression of GAD67. Since no antibody specific to GAD67 was available, this induction was studied using in situ RNA hybridization (FIGS. 6I, 6J and 6K). Although only 5/28 experiments showed a clear induction of GAD67 by Dlx2, this is an under-estimate, as most of the negative experiments were performed during early stages of the project, when the protocol was being established and often low levels of electroporation were encountered. The final three experiments show GAD67 induction by Dlx2.

Thus, these experiments indicate that Dlx2 and Dlx5 are efficient inducers of a fundamental element of the GABAergic phenotype in cortical cells. On the other hand, Dlx2 and Dlx5 failed to clearly induce to detectable levels other markers that are characteristic of basal telencephalic neurons or cortical interneurons such as NPY, nNOS, substance P, enkephalin, OCT-6, calretinin, or calbindin, although none of these shows as close a temporal or spatial correlation during development to Dlx expression as do the GAD genes. Furthermore, ectopic expression of the DLX proteins did not seem to affect expression of TBR1, a transcription factor that marks most early cortical plate neurons (Hevner et al. (2001) Neuron 29:353–366).

Dlx Genes are Regulated by DLX Proteins

Previous loss of function studies provided evidence that Dlx1 and Dlx2 together regulate Dlx5 and Dlx6 in most of the forebrain. In addition, an intergenic enhancer for mouse Dlx5 and Dlx6 and zebrafish dlx4 and dlx6 is regulated by Dlx1 and Dlx2 in transgenic mice and in tissue culture cells. The gain of function assay was utilized to test whether ectopic expression of Dlx1, Dlx2 and/or Dlx5 is sufficient to induce expression from endogenous Dlx genes and from a co-electroporated Dlx5/6 enhancer/reporter plasmid (mI5/6i-LacZ).

Electroporation of Dlx2 in the cortex induced Dlx5 RNA, as judged by in situ hybridization (FIGS. 6I, 6J, and 6L). Although the efficiency of this induction was not robust (4 of 23), this is believed to be an underestimate for the same reasons discussed above regarding the induction of GAD67. Electroporation of Dlx1 did not induce expression of the endogenous Dlx5 gene (data not shown). Induction of Dlx6 expression was not detected following electroporation with either Dlx1, Dlx2 or Dlx5 (data not shown), nor with binary combinations of these expression vectors (n=28).

Finally, it was determined whether the Dlx expression vectors could induce expression from a co-electroporated mI5/6i-LacZ enhancer/reporter plasmid. The electroporations were performed at various rostrocaudal and dorsoventral positions of the E12.5 brain, and patterns were assessed for -galactosidase through immunohistochemistry. Control experiments showed that electroporation of the mI5/6i-LacZ plasmid alone resulted in β-galactosidase expression that was restricted to areas that endogenously express the Dlx genes, such as the ganglionic eminences, septum and ventral thalamus (FIGS. 8A–F). Thus, Dlx5/6 enhancer-mediated expression appears to critically depend on the transcription factors that are present in the Dlx$^+$ regions.

To test whether Dlx2 is sufficient to induce mI5/6i-LacZ expression, the Dlx2 expression vector was co-electroporated with the mI5/6i-LacZ and the GFP expression vectors into the cerebral cortex, midbrain and hindbrain. The Dlx2 expression vector induced robust β-galactosidase expression in the cerebral cortex (FIGS. 8H and 8J), the dorsal thalamus (FIG. 8J), the tectum (FIG. 8L) and the hindbrain (n=15). FIG. 8 shows that Dlx expression vectors induce ectopic expression of a Dlx5/6 enhancer/reporter construct. Shown are pair-wise depictions of the same 50 µm free-floating section in green and red fluorescence. The bottom left corner indicates which expression vectors were electroporated. Red fluorescence marks the expression of the reporter protein β-galactosidase. A plasmid encoding an intergenic mouse Dlx5/6 enhancer (mI5/6i) upstream of the reporter gene LacZ is only expressed in regions that endogenously express Dlx genes (e.g., the CGE but not the cortex (FIGS. 8A and 8B); compare GFP and β-galactosidase expression in the telencephalon). mI5/6i-LacZ is also not expressed in all regions caudal to the ventral thalamus, such as the superior colliculus (FIGS. 8C and 8D) or tegmentum (FIGS. 8E and 8F).

Adding the Dlx2 expression vector to the electroporation, leads to strong expression of β-galactosidase in the cortex (FIGS. 8G, 8H, 8I and 8J), dorsal thalamus (FIGS. 8I and 8J) and in all mid- and hindbrain regions, e. g. the superior colliculus (FIGS. 8K and 8L). The Dlx5 expression vector also leads to expression of the reporter protein in the superior colliculus (FIGS. 8M and 8N) and the pons (FIGS. 8Q and 8R). The Dlx1 expression vector leads to expression of the reporter protein in the pons (FIGS. 8S and 8T), but not in the superior colliculus (FIGS. 8O and 8P). FIGS. 8Q and 8R are rotated 90° counterclockwise, so that dorsal is to the right. Abbreviations used in the figure are: CGE, caudal ganglionic eminence; Cx, cortex; DT, dorsal thalamus; Po, pons; 5C, superior colliculus; and VTe, ventral tegmental area. Scale bars in FIG. 8A and FIG. 8C are 26 µm.

Co-expression of GFP and β-galactosidase regularly exceeded 90% in these experiments (FIG. 8), showing that Dlx2 induction of expression from mI5/6i-LacZ was very efficient. This result also shows that mixtures of three different plasmids are efficiently electroporated into the same cells.

While the Dlx5 expression vector was also a potent inducer of β-galactosidase expression throughout the brain (FIGS. 8N and 8R; n=15), the Dlx1 expression vector produced a different result from the Dlx2 and Dlx5 vectors. Dlx1 induced relatively less β-galactosidase expression in the cerebral cortex (not shown) and the tectum (FIG. 8P). On the other hand, the Dlx1 vector was capable of inducing β-galactosidase in the dorsal thalamus, the tegmentum (ventral midbrain), and in the hindbrain (FIG. 8T) (n=8).

Dlx and GAD expression in the embryonic forebrain is nearly identical. In addition, ectopic expression of a subset of Dlx genes in developing cortical cortex is sufficient to induce the GAD genes. The Dlx genes are sufficient to induce the fundamental phenotype of GABAergic neurons. The results support the hypothesis that the Dlx genes play a significant role in the specification of telencephalic GABAergic neurons (e.g., the projection neurons of the basal ganglia and interneurons of the cortex). Furthermore, these findings may also prove useful for engineering GABAergic neurons from appropriate progenitor cells.

This gain of function study complements the analysis of the Dlx1 and 2 loss of function double mutants, which show differentiation and migration defects in the development of most telencephalic GABAergic neurons (Anderson et al. (1999) Cereb. Cortex 9:646–654). Despite the severe block in GABAergic neuron development in the Dlx1 and 2 mutants, which includes decreased expression of Dlx5 and Dlx6, GAD expression persists, showing that other transcription factors are also capable of regulating GAD expression in the forebrain.

This analysis dissects the specific roles for the Dlx genes in the development of GABAergic neurons. While the genes can induce both GAD65 and GAD67 within 20 hours, no evidence was found showing induction of other markers of GABAergic projection neurons (e.g., enkephalin and substance P) or of GABAergic interneurons (e.g., calbindin and nNOS) (data not shown). Alternatively, cortical cells may not be fully competent to express all genes found in GABAergic neurons, as other transcription factors may be needed in parallel, or in conjunction with, the DLX proteins.

While Dlx2 and Dlx5 were robust inducers of GADs, Dlx1 was not so robust. Dlx genes fall into two major homology groups: Type A (Dlx2, 3 and 5) and Type B (Dlx1, 6 and 7) (Stock et al. (1996) Proc. Natl. Acad. Sci. USA 93:10858–10863; and Liu et al. (1997) Dev. Dyn. 210:498–512). The results show biochemical differences in the functions of A and B subtypes. Furthermore, while Dlx2 and Dlx5 efficiently transactivated expression from a co-electroporated Dlx5/6 enhancer/reporter plasmid in every CNS region tested (FIGS. 8H, 8J, 8L, 8N, and 8R), Dlx1 appeared more restricted in its ability to activate the Dlx5/6 enhancer. For example, while Dlx1 activated Dlx5/6 enhancer expression in the ventral midbrain (tegmentum) and in the ventral hindbrain (FIG. 8T), no effect of Dlx1 on the Dlx5/6 enhancer in the dorsal midbrain (superior colliculus) (FIG. 8P) was observed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of producing a GABAergic cell in vitro, the method comprising:

introducing into an immature neuronal cell a polynucleotide encoding a human DLX2 polypeptide, said introducing allowing for expression of DLX2 in the cell;

wherein expression of DLX2 in the cell results in development of a GABAergic phenotype in the cell, and wherein the GABAergic phenotype is selected from gamma amino butyric acid production, expression of GAD65, and expression of GAD67.

2. The method of claim 1, wherein the polynucleotide is present as an episomal element.

3. The method of claim 1, wherein the polynucleotide is provided in a viral vector.

4. An isolated GABAergic cell produced by the method of claim 1.

5. A method of producing a GABAergic cell in vitro, the method comprising:

contacting an immature human neuronal cell with a DLX2 activity increasing agent selected from a full-length DLX2 protein, a polynucleotide encoding a full-length DLX2 protein. a sonic hedgehog protein, a polynucleotide encoding a sonic hedgehog protein, and a basic fibroblast growth factor, said contacting resulting in an increase in DLX2 activity in the cell relative to DLX2 activity in the cell prior to said contacting;

wherein the increase in DLX2 activity in the cell results in development of a GABAergic phenotype in the cell, and wherein the GABAergic phenotype is selected from gamma amino butyric acid production, expression of GAD65, and expression of GAD67.

6. An isolated GABAergic cell produced by the method of claim 5.

7. A method of identifying an agent that modulates activity of a GABAergic cell, the method comprising:

contacting an isolated GABAergic cell produced by the method of claim 5 with a candidate agent; and detecting an alteration in an activity of the GABAergic cell relative to an untreated GABAergic cell, wherein said activity is selected from production of gamma amino butyric acid. expression of GAD65 . and expression of GAD67;

wherein detection of an alteration in the GABAergic cell is indicative of activity of the candidate agent in modulating the GABAergic cell activity.

* * * * *